(12) United States Patent
Schröder

(10) Patent No.: US 12,344,569 B2
(45) Date of Patent: Jul. 1, 2025

(54) PROCESS FOR MAKING A CONJUGATED DIENE FROM AN ALLYL ALCOHOL

(71) Applicant: Givaudan SA, Vernier (CH)

(72) Inventor: Fridtjof Schröder, Hettlingen (CH)

(73) Assignee: Givaudan SA, Vernier (CH)

(*) Notice: Subject to any disclaimer, the term of this patent is extended or adjusted under 35 U.S.C. 154(b) by 114 days.

(21) Appl. No.: 17/998,531

(22) PCT Filed: Jun. 15, 2021

(86) PCT No.: PCT/EP2021/066156
§ 371 (c)(1),
(2) Date: Nov. 11, 2022

(87) PCT Pub. No.: WO2021/255052
PCT Pub. Date: Dec. 23, 2021

(65) Prior Publication Data
US 2023/0322645 A1  Oct. 12, 2023

(30) Foreign Application Priority Data
Jun. 17, 2020  (GB) ........................... 2009189

(51) Int. Cl.
*C07C 1/213*   (2006.01)
*B01J 31/22*   (2006.01)
*B01J 31/24*   (2006.01)

(52) U.S. Cl.
CPC ........... *C07C 1/213* (2013.01); *B01J 31/2208* (2013.01); *B01J 31/2409* (2013.01); *B01J 31/2457* (2013.01); *B01J 2231/005* (2013.01); *B01J 2531/824* (2013.01); *C07C 2523/44* (2013.01)

(58) Field of Classification Search
CPC ... C07C 1/213; C07C 2523/44; C07C 1/2078; C07C 67/297; C07C 68/06; C07C 67/08; B01J 31/2208; B01J 31/2409; B01J 31/2457; B01J 2231/005; B01J 2531/824
USPC ........................................................ 585/600
See application file for complete search history.

(56) References Cited

U.S. PATENT DOCUMENTS

2019/0381489 A1* 12/2019 Hosaka ................. B01J 37/04

FOREIGN PATENT DOCUMENTS

| JP | H10231255 A | 9/1998 | |
|----|-------------|--------|---|
| JP | 2006327960 A | 12/2006 | |
| JP | 2002121222 A | 4/2022 | |
| WO | 2019057599 A1 | 3/2019 | |
| WO | WO-2019170712 A1 * | 9/2019 | ............. C07C 1/213 |

OTHER PUBLICATIONS

International Search Report for App. No. PCT/EP2021/066156 dated Sep. 27, 2021.
Written Opinion for App. No. PCT/EP2021/066156 dated Sep. 27, 2021.
Great Britain Search Report for App. No. 2009189.8 dated Dec. 8, 2020.
Karoline A. Ostrowski, et al., A general and efficient method for the palladium-catalysed conversion of allylic alcohols into their corresponding dienes, Catalysis Science & Technology, Royal Society of Chemistry, 2016, pp. 1302-1305, vol. 6, Issue 5.
Jean-Pierre Barras, et al., Recent Optimization Highlights of the Georgywood Process, Process Chemistry, Chimia, 2006, pp. 574-579, vol. 60, Issue 9.
D. Srinivas Reddy, et al., Enantioselective Conversion of Oligoprenol Derivatives to Macrocycles in the Germacrene, Cembrene, and 18-Membered Cyclic Sesterterpene Series, Journal of the American Chemical Society, Nov. 22, 2018, pp. 16909-16913, vol. 140, ACS Publications.
Daniele Fiorito, et al., A General Nickel-Catalyzed Kumada Vinylation for the Preparation of 2-Substituted 1,3-Dienes, ACS Catalysis, Jan. 5, 2018, pp. 1392-1398, vol. 8, ACS Publications.
E.J. Smutny, Oligomerization and Dimerization of Butadiene under Homogeneous Catalysis. Reaction with Nucleophiles and the Synthesis of 1,3,7-Octariene, Communications to the Editor, Journal of the American Chemical Society, Dec. 6, 1967, pp. 6793-6794, vol. 89, Issue 25.
Ni Peizhou, "Organic Chemistry", People's Medical Publishing House, 1st Edition in Dec., 1978, which was published on Nov. 30, 1999, pp. 305-306.
Jiro Tsuji, et al., "Formation of a Terminal Conjugated Diene System By The Palladium Catalyzed Elimination Reaction of Allylic Acetates And Phenyl Ethers", Tetrahedron Lett., No. 24, Apr. 14, 1978, pp. 2075-2078.
Tadakatsu Mandai, et al., "A Novel Preparative Method for Homo- and Heteroannular Conjugated Dienes in Decalin Derivatives by the Palladium-Catalyzed Regioselective Elimination Reaction of Allylic Carbonates under Mild Conditions", Tetrahedron Letters, vol. 33, No. 18, Feb. 5, 1992, pp. 2549-2552.
A. K. Bakkestuen et al., "Synthesis and antimycobacterial activity of agelasine E and analogs"; Org. Biomol. Chem, Feb. 9, 2005, pp. 1025-1033.
M. Grinco et al., "A biomimetic synthesis of sacculatane diterpenoids"; Helvetica Chimica Acta, vol. 91, 2008, pp. 249-258.
Mike Dischmann, et al., Chem. Eur. J., Total Synthesis of Isoquinocyclinone, Jul. 22, 2014, pp. 11300-11302.

* cited by examiner

Primary Examiner — Prem C Singh
Assistant Examiner — Francis C Campanell
(74) Attorney, Agent, or Firm — Curatolo Sidoti & Trillis Co., LPA; Floyd Trillis, III; Salvatore A. Sidoti

(57) ABSTRACT

An in-situ method for making a conjugated diene from an allyl alcohol comprising the conversion of the allyl alcohol to an allyl carbonate, allyl ester or allyl formate with concomitant or subsequent conversion of the allyl carbonate, allyl ester or allyl formate to the conjugated diene; the products obtained by said method, and the uses of said products.

16 Claims, No Drawings

PROCESS FOR MAKING A CONJUGATED DIENE FROM AN ALLYL ALCOHOL

CROSS REFERENCE TO RELATED APPLICATIONS

This application is a national stage application of International Application No. PCT/EP2021/066156, filed 15 Jun. 2021, which claims priority from Great Britain Patent Application No. 2009189.8, filed 17 Jun. 2020, both of which applications are incorporated herein by reference.

TECHNICAL FIELD

The present invention relates generally to an in-situ method for making a conjugated diene from an allyl alcohol comprising the conversion of the allyl alcohol to an allyl carbonate, allyl ester or allyl formate followed by conversion of the allyl carbonate, allyl ester or allyl formate to the conjugated diene. The present invention further relates to the conjugated dienes obtained by and/or obtainable by said method and the uses of said conjugated dienes, particularly for the formation of fragrance ingredients.

BACKGROUND

Conjugated dienes frequently serve as substrates for conversion to highly functionalized products via numerous organic reactions such as Diels-Alder reactions, hydroformylation, carbonylation, and cyclopropanation.

For this purpose, conjugated dienes have been prepared directly from allyl alcohols by elimination under relatively harsh reaction conditions such as high temperature and basic or acidic conditions. However, these direct elimination reactions lack selectivity, especially when the number of $R_1$ groups of formula (I) herein that are not hydrogen is more than one, thus resulting in regioisomer mixtures of conjugated dienes, including oligomerization and cyclization by-products.

Transition metal catalyzed elimination of allyl carbonates, allyl esters or allyl formates to form conjugated dienes can improve yield and selectivities compared to the direct elimination of the allyl alcohols under harsh conditions (see, for example, J.-P.Barras, B.Bourdin and F.Schröder, *Chimia* 60, 574, 2006). However, it is first necessary to form the allyl carbonate, allyl ester or allyl formate, for example from an allyl alcohol, before the transition metal catalyzed elimination can take place. This is a disadvantage, particularly in an industrial environment, because additional isolation and purification steps are required before the conjugated diene is formed.

The examples of JP2006327960 disclose the direct elimination of 2,7-octadiene-1-ol to 1,3,7-octatriene in the presence of Pd(OAc)$_2$ and triphenylphosphine in a continuous process by feeding the allyl alcohol continuously to the catalyst and ligand with concomitant distillation of the conjugated diene at temperatures ranging from 120° C. to 230° C. However, regioisomer by-products can be expected from allyl alcohols with a higher substitution pattern than 2,7-octadiene-1-ol (i.e. the number of $R_1$ groups of formula (I) herein that are not hydrogen is more than one). Further, the distillation of the conjugated diene products may be difficult due to the similarity of the allyl alcohol and conjugated diene boiling points. No intermediate compounds are formed in this reaction.

Verholt et al., Cat. Sci. & Tech., 6, 1302, 2016 describes the elimination of allyl alcohols in the presence of catalytic amounts of Pd(acac)$_2$, xantphos and trifluroacetic acid (TFA) in toluene at 105° C. However, relatively high catalyst loadings of 1% are used and a carbon monoxide pressure of 10-40 bar is necessary. The use of carbon monoxide under pressure and corrosive TFA is a disadvantage, particularly in an industrial environment, because of the toxicity of the reactants and the fact that the conjugated diene products cannot be removed continuously from the reaction mixture by distillation.

It is therefore desirable to provide new or improved methods for making conjugated dienes, for example which may provide a more direct conversion of allyl alcohols to conjugated dienes.

SUMMARY

In accordance with a first aspect of the present invention there is provided a method for the in-situ formation of a conjugated diene of formula (III) from an allyl alcohol of formula (I), the method comprising conversion of the allyl alcohol of formula (I)

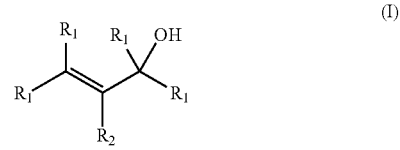

to an allyl carbonate, allyl ester or allyl formate of formula (II)

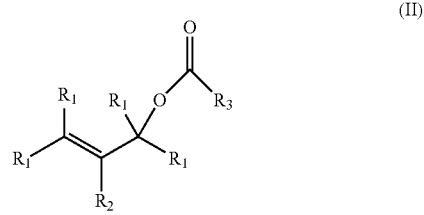

in the presence of a base followed by conversion of the allyl carbonate, allyl ester or allyl formate of formula (II) to the conjugated diene of formula (III)

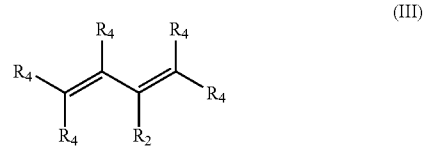

using a palladium catalyst or catalyst precursor and an organic phosphorous ligand, wherein
  each $R_1$ is independently selected from H, alkyl, substituted alkyl, alkenyl, substituted alkenyl, aromatic hydrocarbon, and substituted aromatic hydrocarbon;
  $R_2$ is selected from H, alkyl, substituted alkyl, alkenyl, substituted alkenyl, aromatic hydrocarbon, and substituted aromatic hydrocarbon;
  $R_3$ is selected from H, alkyl, substituted alkyl, alkoxy, substituted alkoxy, phenyl and substituted phenyl;

each $R_4$ is independently selected from H, alkyl, substituted alkyl, alkenyl, substituted alkenyl, aromatic hydrocarbon, and substituted aromatic hydrocarbon;

wherein at least one $R_1$ bears a proton in α-position of the allylic C3 group which is deprotonated under basic reaction conditions thus forming a diene of formula (III) via 1,2 or 1,4 elimination and the at least one $R_1$ is alkyl, substituted alkyl, alkenyl, substituted alkenyl, aromatic hydrocarbon, or substituted aromatic hydrocarbon.

In accordance with a second aspect of the present invention there is provided a conjugated diene of formula (III) obtained by and/or obtainable by the method of the first aspect of the present invention.

In accordance with a third aspect of the present invention there is provided a use of a conjugated diene of the second aspect of the present invention to make a fragrance ingredient.

Certain embodiments of any aspect of the present invention may provide one or more of the following advantages:

in-situ method for making conjugated dienes from allyl alcohols;

EZ mixtures of allyl alcohols give E-dienes or dienes with an enriched EZ proportion due to an equilibration of the intermediate Pd-allyl complexes good selectivity for conjugated diene, in particular exo-dienes;

good yield and purity of the desired conjugated diene;

reduction in the number of purification and isolation steps;

milder reaction conditions, e.g. lower temperature, no pressure, no acid (which is detrimental to the stability of the dienes which are prone to carbocationic side reactions)

low catalyst loadings.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION

The present invention is based on the surprising finding that conjugated dienes can be formed in-situ from allyl carbonates or allyl esters or allyl formates prior to work-up and isolation. The present invention is further based on the surprising finding that the in-situ reaction has high selectivity and efficiency and can be effected with similar or even lower catalyst loadings in impure reaction mixtures compared to reaction mixtures of isolated and purified allyl carbonates or allyl esters or allyl formates. It is also surprising that the palladium catalysts and their ligands used for the elimination reaction are not deactivated by impurities which might be present in the mixture. There are some indications that the catalyst system is even more active in these mixtures.

There is therefore provided herein a method for the in-situ formation of a conjugated diene of formula (III) from an allyl alcohol of formula (I), the method comprising conversion of the allyl alcohol of formula (I)

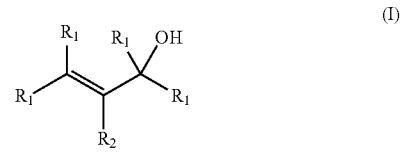

to an allyl carbonate, allyl ester or allyl formate of formula (II)

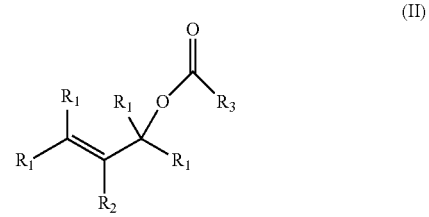

in the presence of a base followed by conversion of the allyl carbonate, allyl ester or allyl formate of formula (II) to the conjugated diene of formula (III)

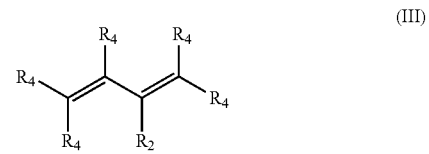

using a palladium catalyst or catalyst precursor and an organic phosphorous ligand, wherein each $R_1$ is independently selected from H, alkyl, substituted alkyl, alkenyl, substituted alkenyl, aromatic hydrocarbon, and substituted aromatic hydrocarbon;

$R_2$ is selected from H, alkyl, substituted alkyl, alkenyl, substituted alkenyl, aromatic hydrocarbon, and substituted aromatic hydrocarbon;

$R_3$ is selected from H, alkyl, substituted alkyl, alkoxy, substituted alkoxy, phenyl and substituted phenyl;

each $R_4$ is independently selected from H, alkyl, substituted alkyl, alkenyl, substituted alkenyl, aromatic hydrocarbon, and substituted aromatic hydrocarbon;

wherein at least one $R_1$ bears a proton in α-position of the allylic C3 group which is deprotonated under basic reaction conditions thus forming a diene of formula (III) via 1,2 or 1,4 elimination and the at least one $R_1$ is alkyl, substituted alkyl, alkenyl, substituted alkenyl, aromatic hydrocarbon, or substituted aromatic hydrocarbon.

As used herein the phrase "in-situ formation of a conjugated diene of formula (III) from an allyl alcohol of formula (I)" refers to a method wherein the entire reaction takes place in a single reaction mixture and any intermediate compounds that are formed (e.g. the allyl carbonate or allyl ester or allyl formate of formula (II)) are not isolated or purified before the subsequent steps are carried out to form the final product (i.e. the conjugated diene of formula (III)). In other words, the conversion of the allyl alcohol of formula (I) to an allyl carbonate, allyl ester or allyl formate of formula (II) in the presence of a base and the conversion of the allyl carbonate, allyl ester or allyl formate of formula (II) to the conjugated diene of formula (III) takes place in the same reaction mixture without isolation or purification of the allyl carbonate, allyl ester or allyl formate of formula (II).

As used herein, the term "alkyl" refers to a radical derived from a saturated cyclic, linear or branched hydrocarbon by removal of a hydrogen atom. For example, the alkyl may be derived from a saturated linear or branched hydrocarbon by removal of a hydrogen atom. Each alkyl may, for example, independently comprise from 1 to 16 carbon atoms. For example, each alkyl may independently comprise from 1 to 12 carbon atoms or from 1 to 10 carbon atoms or from 1 to 8 carbon atoms or from 1 to 6 carbon atoms or from 1 to 5 carbon atoms or from 1 to 4 carbon atoms or from 1 to 3 carbon atoms or from 1 to 2 carbon atoms. For example, each alkyl may independently comprise from 2 to 16 carbon atoms or from 2 to 12 carbon atoms or from 2 to 10 carbon atoms or from 2 to 8 carbon atoms or from 2 to 6 carbon atoms or from 2 to 5 carbon atoms or from 2 to 4 carbon atoms or from 2 to 3 carbon atoms. For example, each alkyl may independently comprise from 3 to 16 carbon atoms or from 3 to 12 carbon atoms or from 3 to 10 carbon atoms or from 3 to 8 carbon atoms or from 3 to 6 carbon atoms or from 3 to 5 carbon atoms or from 3 to 4 carbon atoms.

As used herein, the term "substituted alkyl" refers to a radical derived from a saturated cyclic, linear or branched hydrocarbon by removal of a hydrogen atom, wherein one or more of the remaining hydrogen atoms on the saturated hydrocarbon is replaced by a functional group (also referred to herein as a substituent). For example, the substituted alkyl may be derived from a saturated linear or branched hydrocarbon by removal of a hydrogen atom, wherein one or more of the remaining hydrogen atoms on the saturated hydrocarbon is replaced by a functional group (also referred to herein as a substituent). The substituted alkyl may, for example, have one, two, three, four or five functional groups. The substituted alkyl may, for example, have one or two functional groups.

Each substituted alkyl may, for example, independently comprise from 1 to 16 carbon atoms (not including any carbon atoms present in the functional groups). For example, each substituted alkyl may independently comprise from 1 to 12 carbon atoms or from 1 to 10 carbon atoms or from 1 to 8 carbon atoms or from 1 to 6 carbon atoms or from 1 to 5 carbon atoms or from 1 to 4 carbon atoms or from 1 to 3 carbon atoms or from 1 to 2 carbon atoms (not including any carbon atoms present in the functional groups). For example, each substituted alkyl may independently comprise from 2 to 16 carbon atoms or from 2 to 12 carbon atoms or from 2 to 10 carbon atoms or from 2 to 8 carbon atoms or from 2 to 6 carbon atoms or from 2 to 5 carbon atoms or from 2 to 4 carbon atoms or from 2 to 3 carbon atoms (not including any carbon atoms present in the functional groups). For example, each substituted alkyl may independently comprise from 3 to 16 carbon atoms or from 3 to 12 carbon atoms or from 3 to 10 carbon atoms or from 3 to 8 carbon atoms or from 3 to 6 carbon atoms or from 3 to 5 carbon atoms or from 3 to 4 carbon atoms (not including any carbon atoms present in the functional groups).

As used herein, the term "alkenyl" refers to a radical derived from an unsaturated cyclic, linear or branched hydrocarbon by removal of a hydrogen atom. For example, the alkenyl may be derived from an unsaturated linear or branched hydrocarbon by removal of a hydrogen atom. "Alkenyl" does not encompass aromatic hydrocarbons described below. The alkenyl may, for example, have one, two, or three carbon-carbon double bonds. For example, the alkenyl may have one carbon-carbon double bond. Each alkenyl may, for example, independently comprise from 2 to 12 carbon atoms. For example, each alkenyl may independently comprise from 2 to 10 carbon atoms or from 2 to 8 carbon atoms or from 2 to 6 carbon atoms or from 2 to 5 carbon atoms or from 2 to 4 carbon atoms or from 2 to 3 carbon atoms. For example, each alkenyl may independently comprise from 3 to 12 carbon atoms or from 3 to 10 carbon atoms or from 3 to 8 carbon atoms or from 3 to 6 carbon atoms or from 3 to 5 carbon atoms or from 3 to 4 carbon atoms (not including any carbon atoms present in the functional groups).

As used herein, the term "substituted alkenyl" refers to a radical derived from an unsaturated cyclic, linear or branched hydrocarbon by removal of a hydrogen atom, wherein one or more of the remaining hydrogen atoms on the unsaturated hydrocarbon is replaced by a functional group (also referred to herein as a substituent). For example, the substituted alkenyl may be derived from an unsaturated linear or branched hydrocarbon by removal of a hydrogen atom, wherein one or more of the remaining hydrogen atoms on the unsaturated hydrocarbon is replaced by a functional group (also referred to herein as a substituent). "Substituted alkenyl" does not encompass aromatic hydrocarbons described below. The substituted alkenyl may, for example, have one, two, or three carbon-carbon double bonds. For example, the substituted alkenyl may have one carbon-carbon double bond. The substituted alkenyl may, for example, have one, two, three, four or five functional groups. The substituted alkenyl may, for example, have one or two functional groups.

Each substituted alkenyl may, for example, independently comprise from 2 to 12 carbon atoms (not including any carbon atoms present in the functional groups). For example, each substituted alkenyl may independently comprise from 2 to 10 carbon atoms or from 2 to 8 carbon atoms or from 2 to 6 carbon atoms or from 2 to 5 carbon atoms or from 2 to 4 carbon atoms or from 2 to 3 carbon atoms (not including any carbon atoms present in the functional groups). For example, each substituted alkenyl may independently comprise from 3 to 12 carbon atoms or from 3 to 10 carbon atoms or from 3 to 8 carbon atoms or from 3 to 6 carbon atoms or from 3 to 5 carbon atoms or from 3 to 4 carbon atoms (not including any carbon atoms present in the functional groups).

As used herein, the term "aromatic hydrocarbon" refers to a radical derived from a hydrocarbon group comprising an unsaturated ring of resonance bonds by removal of a hydrogen atom. The aromatic hydrocarbon may, for example, comprise one or more heteroatoms (e.g. one or more of oxygen, nitrogen or sulfur). Alternatively, the aromatic hydrocarbon may not comprise any heteroatoms (i.e. comprises only carbon and hydrogen atoms). The aromatic hydrocarbon radical may, for example, be derived from benzene ($C_6H_6$), toluene ($C_6H_5CH_3$), ethylbenzene ($C_6H_5CH_2CH_3$), xylene ($C_6H_4(CH_3)_2$), mesitylene (($C_6H_3(CH_3)_3$), durene ($C_6H_2(CH_3)_4$), biphenyl ($C_6H_5$-$C_6H_5$), naphthalene ($C_{10}H_8$), furane, thiofurane, pyrazole, imidazole, isoxazole, oxazole, isothiazole or thiazole. For example, the aromatic hydrocarbon may be derived from benzene or toluene or naphthalene. The aromatic hydrocarbon may, for example, comprise from 3 to 12 carbon atoms or from 3 to 10 carbon atoms or from 3 to 8 carbon atoms or from 3 to 6 carbon atoms. For example, the aromatic hydrocarbon may comprise from 4 to 12 carbon atoms or from 4 to 10 carbon atoms or from 4 to 8 carbon atoms or from 4 to 6 carbon atoms. For example, the aromatic hydrocarbon may comprise from 6 to 12 carbon atoms or from 6 to 10 carbon atoms or from 6 to 8 carbon atoms.

As used herein, the term "substituted aromatic hydrocarbon" refers to a radical derived from a hydrocarbon group comprising an unsaturated ring of resonance bonds by removal of a hydrogen atom, wherein one or more of the remaining hydrogen atoms on the unsaturated hydrocarbon is replaced by a functional group (also referred to herein as a substituent). The substituted aromatic hydrocarbon may, for example, comprise one or more heteroatoms in the ring of resonance bonds (e.g. one or more of oxygen, nitrogen or sulfur). Alternatively, the substituted aromatic hydrocarbon may not comprise any heteroatoms in the ring of resonance bonds (i.e. comprises only carbon and hydrogen atoms). The substituted aromatic hydrocarbon radical may, for example, be derived from substituted benzene ($C_6H_6$), substituted toluene ($C_6H_5CH_3$), substituted ethylbenzene ($C_6H_5CH_2CH_3$), substituted xylene ($C_6H_4(CH_3)_2$), substituted mesitylene (($C_6H_3(CH_3)_3$), substituted durene ($C_6H_2(CH_3)_4$), substituted biphenyl ($C_6H_5$-$C_6H_5$), substituted naphthalene ($C_{10}H_8$), substituted furane, substituted thiofurane, substituted pyrazole, substituted imidazole, substituted isoxazole, substituted oxazole, substituted isothiazole or substituted thiazole. For example, the substituted aromatic hydrocarbon may be derived from substituted benzene or substituted toluene or substituted naphthalene. The substituted aromatic hydrocarbon may, for example, have one, two, three, four or five functional groups. The substituted aromatic hydrocarbon may, for example, have one or two functional groups.

The substituted aromatic hydrocarbon may, for example, comprise from 3 to 12 carbon atoms or from 3 to 10 carbon atoms or from 3 to 8 carbon atoms or from 3 to 6 carbon atoms (not including any carbon atoms present in the functional groups). For example, the substituted aromatic hydrocarbon may comprise from 4 to 12 carbon atoms or from 4 to 10 carbon atoms or from 4 to 8 carbon atoms or from 4 to 6 carbon atoms (not including any carbon atoms present in the functional groups). For example, the substituted aromatic hydrocarbon may comprise from 6 to 12 carbon atoms or from 6 to 10 carbon atoms or from 6 to 8 carbon atoms (not including any carbon atoms present in the functional groups).

As used herein, the term "alkoxy" refers to a group having the formula "—OR", wherein R is an alkyl group. The alkyl in the alkoxy group may be as described herein. The alkyl in the alkoxy group may, for example, be a saturated linear or branched chain hydrocarbon. The alkyl in the alkoxy group may, for example, comprise from 1 to 8 carbon atoms or from 1 to 6 carbon atoms or from 1 to 4 carbon atoms or from 1 to 3 carbon atoms or from 1 to 2 carbon atoms.

As used herein, the term "substituted alkoxy" refers to a group having the formula "—OR", wherein R is a substituted alkyl group. The substituted alkyl in the alkoxy group may be as described herein. The substituted alkyl in the alkoxy group may, for example, be a saturated linear or branched chain hydrocarbon wherein one or more of the hydrogen atoms of the hydrocarbon is replaced by a functional group (also referred to herein as a substituent). The substituted alkyl in the substituted alkoxy group may, for example, comprise from 1 to 8 carbon atoms or from 1 to 6 carbon atoms or from 1 to 4 carbon atoms or from 1 to 3 carbon atoms or from 1 to 2 carbon atoms. The substituted alkoxy may, for example, have one, two, three, four or five functional groups. The substituted alkoxy may, for example, have one or two functional groups.

Each functional group (substituent) on the substituted alkyl or substituted alkenyl or substituted aromatic hydrocarbon or substituted alkoxy or substituted phenyl may, for example, independently be selected from a hydroxyl group (—OH), an alkoxy group (—OR wherein R is alkyl including cyclic ethers such as epoxides, oxetanes, tetrahydrofuranes, tetrahydropyranes and oxepanes, all optionally substituted), an amino group (—NR, wherein each R is independently hydrogen or alkyl), a nitro group (—$NO_2$), an acyl group (—CO—R, wherein R is hydrogen or alkyl), an ester group (—O—CO—R, wherein R is alkyl), an alkoxycarbonyl group (—CO—O—R, wherein R is alkyl), an aryloxy group (—O—R, wherein R is an aromatic hydrocarbon), a halogen (e.g. F, Cl, Br or I), and an aromatic hydrocarbon group. In certain embodiments, each functional group on the substituted alkyl or substituted alkenyl or substituted aromatic hydrocarbon or substituted alkoxy may be hydroxyl (—OH).

Where relevant, each functional group may, for example, independently comprise from 1 to 12 carbon atoms. For example, each functional group may independently comprise from 1 to 10 carbon atoms or from 1 to 8 carbon atoms or from 1 to 6 carbon atoms or from 1 to 5 carbon atoms or from 1 to 4 carbon atoms or from 1 to 3 carbon atoms or from 1 to 2 carbon atoms.

The compound of formula (I) is an allyl alcohol. The term "allyl alcohol" as used herein refers to a compound of formula (I) which comprises at least one double bond and at least one alcohol (—OH) group in the α-position of the double bond.

Each $R_1$ is independently selected from hydrogen (H), alkyl, substituted alkyl, alkenyl, substituted alkenyl, aromatic hydrocarbon, and substituted aromatic hydrocarbon, wherein at least one $R_1$ is alkyl, substituted alkyl, alkenyl, substituted alkenyl, aromatic hydrocarbon, or substituted aromatic hydrocarbon (i.e. the at least one $R_1$ is not hydrogen), capable of being deprotonated in the α-position of the allylic C3 group thus forming a conjugated double bond (compound of formula (III)).

For example, each $R_1$ may independently be selected from hydrogen, alkyl, substituted alkyl, alkenyl and substituted alkenyl, wherein at least one $R_1$ is capable of being deprotonated in the α-position of the allylic C3 group thus forming a conjugated double bond (compound of formula (III)), and the at least one $R_1$ is alkyl, substituted alkyl, alkenyl, or substituted alkenyl.

For example, each $R_1$ may independently be selected from hydrogen, alkyl, and alkenyl, wherein at least one $R_1$ is capable of being deprotonated in the α-position of the allylic C3 group thus forming a conjugated double bond (compound of formula (III)), and the at least one $R_1$ is alkyl, or alkenyl.

The $R_1$ groups are not all hydrogen. For example, at least one $R_1$ is alkyl, substituted alkyl, alkenyl, substituted alkenyl, aromatic hydrocarbon or substituted aromatic hydrocarbon, capable of being deprotonated in the α-position of the allylic C3 group thus forming a conjugated double bond (compound of formula (III)). For example, at least one $R_1$ is alkyl, substituted alkyl, alkenyl or substituted alkenyl capable of being deprotonated in the α-position of the allylic C3 group thus forming a conjugated double bond (compound of formula (III)). For example, at least one $R_1$ is alkyl or alkenyl, capable of being deprotonated in the α-position of the allylic C3 group thus forming a conjugated double bond (compound of formula (III)).

For example, at least one $R_1$ may be hydrogen. For example, from one to three $R_1$ groups may be hydrogen. For example, one or two $R_1$ groups may be hydrogen.

For example, at least one $R_1$ may be alkyl or substituted alkyl. For example, from one to three $R_1$ groups may be alkyl or substituted alkyl. For example, one or two $R_1$ groups may be alkyl or substituted alkyl. For example, at least one $R_1$ may be alkyl. For example, from one to three $R_1$ groups may be alkyl. For example, one or two $R_1$ groups may be alkyl.

For example, at least one $R_1$ may be alkenyl or substituted alkenyl. For example, from one to three $R_1$ groups may be alkenyl or substituted alkenyl. For example, one or two $R_1$ groups may be alkenyl or substituted alkenyl. For example, at least one $R_1$ may be alkenyl. For example, from one to three $R_1$ groups may be alkenyl. For example, one or two $R_1$ groups may be alkenyl.

For example, at least one $R_1$ may be hydrogen and at least one $R_1$ may be alkyl or substituted alkyl. For example, at least one $R_1$ may be hydrogen and at least one $R_1$ may be alkyl.

For example, at least one $R_1$ may be hydrogen and at least one $R_1$ may be alkenyl or substituted alkenyl. For example, at least one $R_1$ may be hydrogen and at least one $R_1$ may be alkenyl.

For example, at least one $R_1$ may be hydrogen, at least one $R_1$ may be alkyl or substituted alkyl, and at least one $R_1$ may be alkenyl or substituted alkenyl. For example, at least one $R_1$ may be hydrogen, at least one $R_1$ may be alkyl, and at least one $R_1$ may be alkenyl.

$R_2$ is selected from hydrogen, alkyl, substituted alkyl, alkenyl, substituted alkenyl, aromatic hydrocarbon, and substituted aromatic hydrocarbon. $R_2$ may, for example, be selected from hydrogen, alkyl, substituted alkyl, alkenyl, and substituted alkenyl. $R_2$ may, for example, be selected from hydrogen, alkyl, and alkenyl. $R_2$ may, for example, be hydrogen or alkyl. $R_2$ may, for example, be hydrogen.

The total number of carbon atoms in the allyl alcohol of formula (I) may, for example, be from 4 to 40 (including any carbon atoms present in any functional groups of a substituted alkyl, substituted alkenyl or substituted aromatic hydrocarbon). For example, the total number of carbon atoms in the allyl alcohol of formula (I) may be from 4 to 35 or from 4 to 30 or from 4 to 25 or from 4 to 20 or from 4 to 18 or from 4 to 16 or from 4 to 15 (including any carbon atoms present in any functional groups of a substituted alkyl, substituted alkenyl or substituted aromatic hydrocarbon). For example, the total number of carbon atoms in the allyl alcohol of formula (I) may be from 6 to 40 or from 6 to 35 or from 6 to 30 or from 6 to 25 or from 6 to 20 or from 6 to 18 or from 6 to 16 or from 6 to 15 (including any carbon atoms present in any functional groups of a substituted alkyl, substituted alkenyl or substituted aromatic hydrocarbon). For example, the total number of carbon atoms in the allyl alcohol of formula (I) may be from 8 to 40 or from 8 to 35 or from 8 to 30 or from 8 to 25 or from 8 to 20 or from 8 to 18 or from 8 to 16 or from 8 to 15. For example, the total number of carbon atoms in the allyl alcohol of formula (I) may be from 10 to 40 or from 10 to 35 or from 10 to 30 or from 10 to 25 or from 10 to 20 or from 10 to 18 or from 10 to 16 or from 10 to 15 (including any carbon atoms present in any functional groups of a substituted alkyl, substituted alkenyl or substituted aromatic hydrocarbon).

The compound of formula (I) may, for example, be selected from 2,7-octadiene-1-ol, 3,7,11-trimethyldodeca-1,6,10-trien-3-ol (nerolidol), 4,8-dimethylnona-2,7-dien-4-ol (homolinalool), 3,7-dimethylnona-1,6-dien-3-ol (ethyl linalool), 2,6-dimethyloct-2-ene-1,8-diol, 3,7-dimethyloct-5-ene-1,7-diol, 3,7-dimethyloct-7-ene-1,6-diol, 2,4,8-trimethylnona-2,7-dien-4-ol, 4,8-dimethylnona-3,7-dien-2-ol (methylgeraniol), 3,5-dimethylhex-2-en-1-ol, 6,10-dimethylundeca-1,5,9-trien-4-ol, 6,10-dimethylundeca-5,9-dien-1-yn-4-ol and 1-(3-hydroxy-3-methylpent-4-en-1-yl)-2,5,5,8a-tetramethyl-decahydronaphthalen-2-ol (Sclareol).

The compound of formula (II) is an allyl carbonate, allyl ester or allyl formate. Where $R_3$ is hydrogen, the compound of formula (II) is an allyl formate. Where $R_3$ is alkyl, substituted alkyl, phenyl or substituted phenyl the compound of formula (II) is an allyl ester. Where $R_3$ is alkoxy or substituted alkoxy, the compound of formula (II) is an allyl carbonate.

Each $R_1$ group in the compound of formula (II) is the same as the corresponding $R_1$ group in the compound of formula (I).

The $R_2$ group in the compound of formula (II) is the same as the $R_2$ group in the compound of formula (I).

$R_3$ is selected from hydrogen, alkyl, substituted alkyl, alkoxy, substituted alkoxy, phenyl and substituted phenyl. $R_3$ may, for example, be selected from alkyl, substituted alkyl, alkoxy, substituted alkoxy, and phenyl. $R_3$ may, for example, be selected from alkyl, alkoxy, and phenyl.

Where $R_3$ may be alkyl, the alkyl may, for example, be selected from methyl, ethyl, propyl, isopropyl, n-butyl, and isobutyl.

Where $R_3$ may be alkoxy, the alkoxy may, for example, be selected from methoxy, ethoxy, propoxy, isopropoxy, n-butoxy, and isobutoxy.

The total number of carbon atoms in $R_3$ (including any carbon atoms present in any functional groups of a substituted alkoxy) may, for example, be from 1 to 8. For example, the total number of carbon atoms in $R_3$ (including any carbon atoms present in any functional groups of a substituted alkoxy) may, for example, be from 1 to 6 or from 1 to 4 or from 1 to 3 or from 1 to 2.

The compound of formula (III) is a conjugated diene formed by elimination of the —O—C(O)—$R_3$ group of the compound of formula (II). Therefore, at least two of the $R_4$ groups may be the same as the corresponding $R_1$ groups of the compound of formula (I) and (II). For example, three of the $R_4$ groups may be the same as the corresponding $R_1$ groups of the compound of formula (I) and (II).

The $R_2$ group in the compound of formula (III) is the same as the $R_2$ group in the compound of formula (I).

Each $R_4$ is independently selected from hydrogen (H), alkyl, substituted alkyl, alkenyl, substituted alkenyl, aromatic hydrocarbon, and substituted aromatic hydrocarbon.

For example, each $R_4$ may independently be selected from hydrogen, alkyl, substituted alkyl, alkenyl and substituted alkenyl.

For example, each $R_4$ may independently be selected from hydrogen, alkyl, and alkenyl.

For example, at least one $R_4$ may be hydrogen. For example, from one to three $R_4$ groups may be hydrogen. For example, one or two $R_4$ groups may be hydrogen.

For example, at least one $R_4$ may be alkyl or substituted alkyl. For example, from one to three $R_4$ groups may be alkyl or substituted alkyl. For example, one or two $R_4$ groups may be alkyl or substituted alkyl. For example, at least one $R_4$ may be alkyl. For example, from one to three $R_4$ groups may be alkyl. For example, one or two $R_4$ groups may be alkyl.

For example, at least one $R_4$ may be alkenyl or substituted alkenyl. For example, from one to three $R_4$ groups may be alkenyl or substituted alkenyl. For example, one or two $R_4$ groups may be alkenyl or substituted alkenyl. For example, at least one $R_4$ may be alkenyl. For example, from one to three $R_4$ groups may be alkenyl. For example, one or two $R_4$ groups may be alkenyl.

For example, at least one $R_4$ may be hydrogen and at least one $R_4$ may be alkyl or substituted alkyl. For example, at least one $R_4$ may be hydrogen and at least one $R_4$ may be alkyl.

For example, at least one $R_4$ may be hydrogen and at least one $R_4$ may be alkenyl or substituted alkenyl. For example, at least one $R_4$ may be hydrogen and at least one $R_4$ may be alkenyl.

For example, at least one $R_4$ may be hydrogen, at least one $R_4$ may be alkyl or substituted alkyl, and at least one $R_4$ may be alkenyl or substituted alkenyl. For example, at least one $R_4$ may be hydrogen, at least one $R_4$ may be alkyl, and at least one $R_4$ may be alkenyl.

In one specific embodiment the substitution pattern of the compounds of formula (III) is such that the compound of formula (III) represents a diene comprising an exo-methylene group. By the term "exo-methylene group" is meant a non-terminal $CH_2$ entity attached by a double bond to a carbon chain or ring. As specific examples one may cite homomyrcene (e.g. E-Homomyrcene), ethyl myrcene, 5-methyl-3-methylenehex-1-ene, farnesene (e.g. 6-E-farnesene), 2,8-dimethyl-4-methylenenona-2,7-diene, 10-methyl-6-methyleneundeca-1,4,9-triene (e.g. E-10-methyl-6-methyleneundeca-1,4,9-triene) and 10-methyl-6-methyleneundeca-4,9-dien-1-yne (e.g. E-10-methyl-6-methyleneundeca-4,9-dien-1-yne). In particular this class of dienes can undergo optional subsequent Diels-Alder or 1,4-hydrogenations reactions with good selectivity, resulting in precursors useful in the fragrance industry.

With other words, to provide dienes with an exo-methylene group at least one $R_1$ in formula (I) must be a methyl group, which is selectively deprotonated.

$R_2$ is selected from hydrogen, alkyl, substituted alkyl, alkenyl, substituted alkenyl, aromatic hydrocarbon, and substituted aromatic hydrocarbon. $R_2$ may, for example, be selected from hydrogen, alkyl, substituted alkyl, alkenyl, and substituted alkenyl. $R_2$ may, for example, be selected from hydrogen, alkyl, and alkenyl. $R_2$ may, for example, be hydrogen or alkyl. $R_2$ may, for example, be hydrogen.

The total number of carbon atoms in the conjugated diene of formula (III) may, for example, be from 6 to 40 (including any carbon atoms present in any functional groups of a substituted alkyl, substituted alkenyl or substituted aromatic hydrocarbon). For example, the total number of carbon atoms in the conjugated diene of formula (III) may be from 6 to 35 or from 6 to 30 or from 6 to 25 or from 6 to 20 or from 6 to 18 or from 6 to 16 or from 6 to 15 (including any carbon atoms present in any functional groups of a substituted alkyl, substituted alkenyl or substituted aromatic hydrocarbon). For example, the total number of carbon atoms in the conjugated diene of formula (III) may be from 7 to 40 or from 7 to 35 or from 7 to 30 or from 7 to 25 or from 7 to 20 or from 7 to 18 or from 7 to 16 or from 7 to 15 (including any carbon atoms present in any functional groups of a substituted alkyl, substituted alkenyl or substituted aromatic hydrocarbon). For example, the total number of carbon atoms in the conjugated diene of formula (III) may be from 8 to 40 or from 8 to 35 or from 8 to 30 or from 8 to 25 or from 8 to 20 or from 8 to 18 or from 8 to 16 or from 8 to 15. For example, the total number of carbon atoms in the conjugated diene of formula (III) may be from 10 to 40 or from 10 to 35 or from 10 to 30 or from 10 to 25 or from 10 to 20 or from 10 to 18 or from 10 to 16 or from 10 to 15 (including any carbon atoms present in any functional groups of a substituted alkyl, substituted alkenyl or substituted aromatic hydrocarbon).

The compound of formula (III) may, for example, be 6-E-farnesene, which may, for example, be a α/β-mixture of 6-E-farnesene,

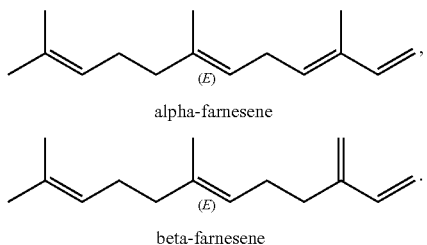

alpha-farnesene beta-farnesene

The compound of formula (III) may, for example, be homomyrcene,

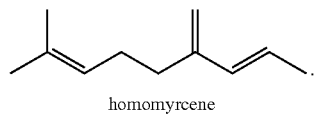

homomyrcene

The compound of formula (III) may, for example, be ethyl myrcene,

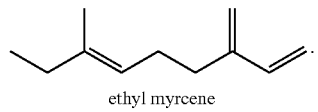

ethyl myrcene

The compound of formula (III) may, for example, be a mixture (e.g. a 1:1 mixture) of

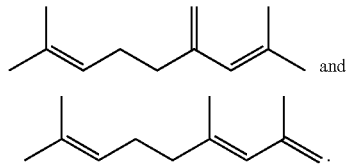

The compound of formula (III) may, for example, be 5-methyl-3-methylenehex-1-ene,

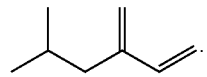

The compound of formula (III) may, for example, be octa-1,3,7-triene

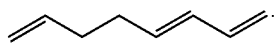

In a further embodiment the compound of formula (III) may, for example, be a compound selected from

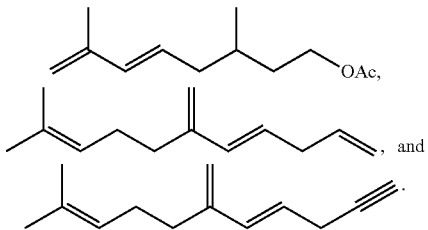

The conversion of the allyl carbonate or allyl ester or allyl formate of formula (II) to the conjugated diene of formula (III) may be concomitant with or subsequent to the conversion of the allyl alcohol of formula (I) to the allyl carbonate, allyl ester or allyl formate of formula (II).

By "concomitant with" it is meant that the reagents for the conversion of the allyl carbonate or allyl ester or allyl formate of formula (II) to the conjugated diene of formula (III) are added to the reaction mixture at the same time as the reagents for the conversion of the allyl alcohol of formula (I) to the allyl carbonate, allyl ester or allyl formate of formula (II) such that both conversion reactions take place in the reaction mixture at the same time. The intermediate allyl carbonate or allyl ester or allyl formate of formula (II) is therefore withdrawn from the equilibrium with the allyl alcohol of formula (I) by elimination and production of the conjugated diene of formula (III).

By "subsequent to" it is meant that at least some of the reagents (e.g. the palladium catalyst or catalyst precursor and/or the organic phosphorous ligand) for the conversion of the allyl carbonate or allyl ester or allyl formate of formula (II) to the conjugated diene of formula (III) are added to the reaction mixture after complete or incomplete conversion of the allyl alcohol of formula (I) to the allyl carbonate, allyl ester or allyl formate of formula (II). Where the conversion of the allyl alcohol of formula (I) to the allyl carbonate, allyl ester or allyl formate of formula (II) was incomplete, addition of the reagents for the conversion of the allyl carbonate, allyl ester or allyl formate of formula (II) to the conjugated diene of formula (III) may result in a period in which both conversion reactions take place in the reaction mixture at the same time. However, there is first a period in which only the conversion of the allyl alcohol of formula (I) to the allyl carbonate, allyl ester or allyl formate of formula (II) is taking place. The subsequent conversion takes place in the same reaction mixture and no isolation or purification of the compound of formula (II) takes place, therefore the subsequent conversion is an in-situ reaction in accordance with the present disclosure.

The conversion of the allyl alcohol of formula (I) to the allyl carbonate, allyl ester or allyl formate of formula (II) and/or the conversion of the allyl carbonate, allyl ester or allyl formate of formula (II) to the conjugated diene of formula (III) may, for example, take place in an inert atmosphere. By "inert atmosphere" it is meant an atmosphere that does not undergo any chemical reactions in the conditions used for the conversion of the allyl alcohol of formula (I) to the allyl carbonate, allyl ester or allyl formate of formula (II) and/or the conversion of the allyl carbonate, allyl ester or allyl formate of formula (II) to the conjugated diene of formula (III).

The conversion of the allyl alcohol of formula (I) to the allyl carbonate, allyl ester or allyl formate of formula (II) and/or the conversion of the allyl carbonate, allyl ester or allyl formate of formula (II) to the conjugated diene of formula (III) may, for example, take place in a noble gas (e.g. argon) or nitrogen atmosphere. The conversion of the allyl alcohol of formula (I) to the allyl carbonate, allyl ester or allyl formate of formula (II) and/or the conversion of the allyl carbonate, allyl ester or allyl formate of formula (II) to the conjugated diene of formula (III) may, for example, take place in a nitrogen atmosphere.

The conversion of the allyl alcohol of formula (I) to the allyl carbonate, allyl ester or allyl formate of formula (II) and/or the conversion of the allyl carbonate, allyl ester or allyl formate of formula (II) to the conjugated diene of formula (III) may, for example, take place under atmospheric pressure (around 101 kPa).

The conversion of the allyl alcohol of formula (I) to the allyl carbonate, allyl ester or allyl formate of formula (II) and/or the conversion of the allyl carbonate, allyl ester or allyl formate of formula (II) to the conjugated diene of formula (III) may, for example, take place at a temperature less than about 120° C. For example, the conversion of the allyl alcohol of formula (I) to the allyl carbonate, allyl ester or allyl formate of formula (II) and/or the conversion of the allyl carbonate, allyl ester or allyl formate of formula (II) to the conjugated diene of formula (III) may, for example, take place at a temperature equal to or less than about 119° C. or equal to or less than about 118° C. or equal to or less than about 117° C. or equal to or less than about 116° C. or equal to or less than about 115° C. The conversion of the allyl alcohol of formula (I) to the allyl carbonate, allyl ester or allyl formate of formula (II) and/or the conversion of the allyl carbonate, allyl ester or allyl formate of formula (II) to the conjugated diene of formula (III) may, for example, take place at a temperature equal to or greater than about 80° C. or equal to or greater than about 90° C. or equal to or greater than about 100° C. or equal to or greater than about 105° C. or equal to or greater than about 110° C. For example, the conversion of the allyl alcohol of formula (I) to the allyl carbonate, allyl ester or allyl formate of formula (II) and/or the conversion of the allyl carbonate, allyl ester or allyl formate of formula (II) to the conjugated diene of formula (III) may, for example, take place at a temperature ranging from about 80° C. to less than about 120° C. or from about 90° C. to less than about 120° C. or from about 100° C. to less than about 120° C. or from about 105° C. to less than about 120° C.

The conversion of the allyl alcohol of formula (I) to the allyl carbonate or allyl ester or allyl formate of formula (II) takes place in the presence of a base.

The base may, for example, be one or more amine(s) or one or more alkoxide(s) or a combination thereof. The amine base may, for example, be a primary, secondary or tertiary amine base. For example, the amine base may be a tertiary amine base. The alkoxide may, for example, be an alkoxide salt.

Bases such as metal hydrides, e.g. LiH, NaH or KH might also be used. However they are less preferred.

Examples of amine bases include, for example, mono-, di-, or tri-alkylamines (e.g. methylamine, ethylamine, butylamine, dimethylamine, diethylamine, dibutylamine, trimethylamine, trimethylamine, tributylamine, substituted and unsubstituted aniline (e.g. N,N-dimethylaniline), and substituted and unsubstituted heterocyclic amines (e.g. pyridine, dimethylaminopyridine, pyrrolidine, pyrrole, purines, imidazole).

Examples of alkoxide bases include, for example, methoxide salts (e.g. sodium methoxide), ethoxide salts, isopropoxide salts, and butoxide salts.

The base may, for example, be selected from triethylamine, tributylamine, dimethylaminopyridine, sodium methoxide, and combinations thereof.

For example, the total amount of base used in the method may range from about 0.1-10 mol %, preferentially 0.3-3% mol % in case of the alkoxides and from about 1-5 mol eq, preferentially 2-3 mol eq in case of the tertiary amines. In case of the alkoxides too low quantities of base may react with traces of water thus inhibiting their reactivities, too large quantities can cause stirring problems. In case of the amines at least 1 mol eq is preferably used to quench the acid, e.g. HOAc, generated after elimination reaction of the allylic acetates (II), too large quantities are economically detrimental because these amines must be usually recycled.

The conversion of the allyl alcohol of formula (I) to the allyl carbonate, allyl ester or allyl formate of formula (II) may take place by reacting the allyl alcohol of the formula (I) with a compound of formula (IV) or a compound of formula (V) in the presence of a base,

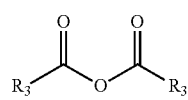
(IV)

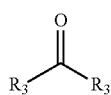
(V)

wherein $R_3$ is as described herein in relation to the compound of formula (II).

Alternatively the conversion of allyl alcohol of formula (I) to the allyl carbonate, allyl ester or allyl formate of formula (II) may take place by reacting the allyl alcohol of the formula (I) with a compound of formula (VI) in the presence of a base

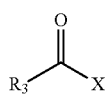
(VI)

wherein X is Cl, or Br.

The compound of formula (IV) may, for example, be acetic anhydride, or dimethyl carbonate.

For example, the compound of formula (IV) may, for example, be used in the method in an amount ranging from about 1-10 mol eq, e.g. acetanhydride, for example in a range from about 2.5-7.5 mol eq, or in a range from about 4.5-5.5 eq. At least about one mol eq anhydride (IV) should be used to convert the allylic alcohol fully to the acetate (II). However, higher amounts might be preferred because the anhydride (IV) could also act like a solvent, allows stirring and accelerates the reaction. However, more than about 10 mol eg of the anhydride (IV) might be uneconomical because the anhydride must be recycled.

For example, the carbonates of formula (V) may, for example, be used in an amount ranging from about 2 to 10 mol eq, for example, about 3 to 5 mol eq.

The conversion of the allyl carbonate, allyl ester or allyl formate of formula (II) to the conjugated diene of formula (III) uses a palladium catalyst or catalyst precursor and an organic phosphorous ligand.

The organic phosphorous ligand assists in providing and maintaining the catalytic activity of the palladium catalyst or catalyst precursor.

The palladium catalyst may, for example, be palladium on carbon (Pd/C) wherein the palladium metal is supported on activated carbon.

The palladium catalyst precursor may, for example be selected from palladium acetate (Pd(OAc)$_2$), palladium bisacetylacetonate (Pd(acac)$_2$), allylpalladium chloride dimer ([(C$_3$H$_5$)PdCl]$_2$), bis(acetonitrile)dichloropalladium (Pd(MeCN)$_2$Cl$_2$), palladium bis(dibenzylideneacetone) (Pd(dba)$_2$), palladium trifluoroacetate (Pd(TFA)$_2$), tris(dibenzylideneacetone) dipalladium (Pd$_2$(dba)$_3$), tetrakis(triphenylphosphine) palladium (Pd(PPh$_3$)$_4$), dichlorobis(tricyclohexylphosphine)palladium (PdCl$_2$[P(cy)$_3$]$_2$), dichlorobis(triphenylphosphine) palladium (Pd(PPh$_3$)$_2$Cl$_2$), dichlorobis(tri-o-tolylphosphine) palladium (Pd[P(o-tol)$_3$]$_2$Cl$_2$]), bis(di-tert)-butyl(4-dimethylaminophenyl)phosphine (Pd(amphos)Cl$_2$), [bis(diphenylphosphino)ferrocene]dichloro palladium (Pd(dppf)Cl$_2$), [bis(di-tert-butylphenylphosphino)ferrocene]dichloro palladium (Pd(dtbpf)Cl$_2$), tetrakis(acetonitrile) palladium tetrafluoroborate (Pd(MeCN)$_4$(BF$_4$)$_2$), palladium bromide (PdBr$_2$), palladium chloride (PdCl$_2$), bis(1,5-cyclooctadiene) palladium (Pd(C$_8$H$_{12}$)$_2$), bis(triphenylphosphine) (maleic anhydride) palladium, tri(di-benzylideneacetone) dipalladium, (1,5-cyclooctadiene) (maleic anhydride) palladium, palladium propionate (Pd(C$_2$H$_5$CO$_2$)$_2$), palladium carbonate (Pd(CO$_3$)), palladium benzoate (Pd(CO$_2$-C$_6$H$_5$)$_2$), palladium sulfate (Pd(SO$_4$)), palladium nitrate (Pd(NO$_3$)$_2$), lithium palladium chloride (Cl$_2$LiPd), bisbenzonitrile palladium chloride (PdCl$_2$(NCC$_6$H$_5$)$_2$), bistriphenylphosphine palladium chloride (PdCl$_2$)(PPh$_3$)$_2$), and bistriphenylphosphine palladium acetate ([(C$_6$H$_5$)$_3$]$_2$Pd(CH$_3$COO)$_2$).

The palladium catalyst precursor may, for example, be a catalyst selected from palladium acetate (Pd(OAc)$_2$), palladium bis(dibenzylideneacetone) (Pd(dba)$_2$), and tetrakis(triphenylphosphine) palladium (Pd(PPh$_3$)$_4$).

The organic phosphorous ligand may, for example, be an organic phosphite ligand, an organic phosphine ligand, an organic phosphonium ligand, an organic phosphinoxide, an organic bisphosphine or a combination thereof.

The organic phosphorous ligand may, for example, be a bidentate organic phosphorous ligand. The bidentate organic phosphorus ligand may be partially oxidized thus containing one phosphine and one phosphin oxide group.

For example, the organic phosphorous ligand may be an organic phosphine ligand. The organic phosphine compound may, for example, be an organic bisphosphine ligand.

Examples of organic phosphite ligands include triethyl phosphite, triisopropyl phosphite, tridecyl phosphite, tridodecyl phosphite, triphenyl phisphite, tris (pt-butylphenyl) phosphite, tris(nonylphenyl) phosphite, trioleyl phosphite, diphenyl monodecyl phosphite, and combinations thereof.

Examples of organic phosphine ligands include xantphos, trimethylphosphine, triethylphosphine, triisopropylphosphine, tri-n-butylphosphine, tri-t-butyl-phosphine, tri-n-hexylphosphine, tri-n-ocylphosphine, tricyclohexylphosphine, triphenylphosphine (TPP or PPh$_3$), dimethylphenylphosphine, methyldiphenylphosphine, ethyldiphenylphosphine, cyclohexyldiphenylphosphine, tri-p-tolylphsphine, tri-o-tolylphosphine, tris(p-chlorophenyl) phosphine, tri(1-naphthyl) phosphine, tris (4-carboxyphenyl) phosphine, tris (4-dimethylaminophenyl) phosphine, lithium diphenylphosphinobenzene-m-sulfonate, tris (o-methoxyphenyl) phosphine, tris (p-methoxyphenyl) phosphine, 1,2-bis (diphenylphosphino) ethane, 1,3-bis (diphenylphosphino) propane, 1,3-bis(di(o-methoxyphenyl) phosphino) propane, 1,4-bis (diphenylphosphino) butane, 1,2-bis(diphenylphosphino) benzene, bis(diphenylphosphino) methane (dppm), bid(diphenylphosphino)hexane (dpph), (oxydi-2,1-phenylene)bis (diphenylphosphine) (DPEphos), 1,5-pentanediylbis[diphenylphosphine] (dpppe), 1,1'-Bis(diphenylphosphino) ferrocene (dppf), 2,2'-bis(diphenylphosphino)-1,1'-binaphthyl (BINAP), 1,2-Bis(diphenylphosphino)ethane (dppe), and combinations thereof.

The palladium catalyst or catalyst precursor may, for example, be used in an amount equal to or less than about 0.5 mol %. For example, the palladium catalyst or catalyst precursor may be used in an amount equal to or less than about 0.4 mol % or equal to or less than about 0.3 mol % or equal to or less than about 0.2 mol % or equal to or less than about 0.1 mol % or equal to or less than about 0.05 mol %.

The palladium catalyst or catalyst precursor may, for example, be used in an amount equal to or greater than about 0.001 mol %. For example, the palladium catalyst or cataylst precursor may be used in an amount equal to or greater than about 0.003 mol % or equal to or greater than about 0.005 mol % or equal to or greater than about 0.01 mol % or equal to or greater than about 0.02 mol % or equal to or greater than about 0.03 mol % or equal to or greater than about 0.04 mol %.

For example, the palladium catalyst or catalyst precursor may be used in an amount ranging from about 0.001 mol % to about 0.5 mol % or from about 0.01 mol % to about 0.2 mol % or from about 0.02 mol % to about 0.1 mol %.

The organic phosphorous ligand may, for example, be used in an amount equal to or less than about 0.25 mol %. For example, the organic phosphorous ligand may be used in an amount equal to or less than about 0.20 mol % or equal to or less than about 0.15 or equal to or less than about 0.10 mol % or equal to or less than about 0.05 mol % or equal to or less than about 0.025 mol %.

The organic phosphorous ligand may, for example, be used in an amount equal to or greater than about 0.002 mol %. For example, the organic phosphorous ligand may be used in an amount equal to or greater than about 0.002 mol % or equal to or greater than about 0.0025 mol % or eqaul to or greater than about 0.005 mol % or equal to or greater than about 0.01 mol % or equal to or greater than about 0.015 or equal to or greater than about 0.02 mol %.

In one particular embodiment the organic phosphorous ligand may be used with at least 2 mol eq monophosphine and at least 1 mol eq bisphosphine ligand/Pd-catalyst.

The yield of the conjugated diene of formula (III) may, for example, be equal to or greater than about 45%. For example, the yield of the conjugated diene of formula (III) may be equal to or greater than about 50% or equal to or greater than about 55% or equal to or greater than about 60% or equal to or greater than about 65% or equal to or greater than about 70% or equal to or greater than about 75% or equal to or greater than about 80% or equal to or greater than about 85% or equal to or greater than about 90%.

The yield of the conjugated diene of formula (III) may, for example, be equal to or less than about 100%. For example, the yield of the conjugated diene of formula (III) may be equal to or less than about 99% or equal to or less than about 98% or equal to or less than about 97% or equal to or less than about 96% or equal to or less than about 95%.

For example, the yield of the conjugated diene of formula (III) may range from about 45% to about 100% or from about 60% to about 100% or from about 80% to about 100% or from about 90% to about 98%.

The purity of the conjugated diene of formula (III) may, for example be equal to or greater than about 75%. For example, the purity of the conjugated diene of formula (III) may be equal to or greater than about 80% or equal to or greater than about 85% or equal to or greater than about 90%.

The purity of the conjugated diene of formula (III) may, for example, be equal to or less than about 100%. For example, the purity of the conjugated diene of formula (III) may be equal to or less than about 99% or equal to or less than about 98% or equal to or less than about 97% or equal to or less than about 96% or equal to or less than about 95%.

For example, the purity of the conjugated diene of formula (III) may range from about 75% to about 100% or from about 80% to about 100% or from about 85% to about 99% or from about 90% to about 98%.

Yield and purity may be measured by gas chromatography, NMR-calibration and HPLC might be other analytical methods.

The method may, for example, be a continuous process wherein the reagents are continually fed to the reaction mixture as the final product (composition comprising the conjugated diene of formula (III) is removed). Alternatively, the method may, for example, be a batch process wherein a specified amount of reagents are fed into the reaction mixture before the reaction is stopped and the final product recovered.

As a specific example one may mention the method using a compound of formula (V) wherein $R_3$ is alkoxy (i.e. a carbonate), the method may be a continuous process wherein the carbonate and/or the base is continuously fed to the reaction mixture whereas the thus formed alcohol or a mixture of this alcohol and carbonate is continuously removed by distillation.

The method may, for example, further comprise isolating and/or purifying the conjugated diene of formula (Ill) from the reaction mixture. The isolating and/or purifying may involve methods known to persons skilled in the art, for example, distillation or column chromatography. Alternatively, the crude diene (III) formed may be subjected as crude or in the work-up solvent to the subsequent reaction.

Work-up solvents are usually inexpensive nonpolar and aprotic solvents, such as hexane, cyclohexane, heptane, tert-butyl methyl ether, toluene or xylene, to dissolve the non-polar products and allow good phase separation. Solvents which form azeotropes with water would be preferred because drying can be performed azeotropically before distillation of diene (III).

Excess reactants (e.g. base and/or compound of formula (IV) or (V)) may, for example, be removed and/or recycled, for example by distillation.

The basic product mixture may, for example, be cooled (e.g. to a temperature ranging from about 5° C. to about 25° C.) and neutralized, for example using a hydrochloric acid solution. Excess acid and too low pH's should be avoided because the dienes (III) formed are usually instable under too acidic conditions. Distillation could therefore be carried out after (careful) neutralization and/or even under slightly basic conditions.

Solvent extraction may be used to separate the conjugated diene of formula (III), for example, using an organic solvent such as tertiary-butyl methyl ether or hexane. The organic layers may then be washed, for example with water, brine and sodium bicarbonate, and optionally dried, for example with magnesium sulphate.

The organic solvent may then be removed and the conjugated diene of formula (III) used as crude or further purified by distillation including wipe-film distillation There is further provided herein the conjugated dienes obtained by and/or obtainable by the methods described herein. The conjugated dienes may, for example, have a yield and/or purity as described herein.

The conjugated dienes prepared according to the present procedure as described hereinabove may, for example, be used as starting materials for the formation of various fragrance ingredients, including Ambrofix™, and Georgywood™.

EXAMPLES

General

GCMS: 50° C./2 min, 20° C./min 240° C., 35° C./min 270° C. Agilent 5975C MSD with HP 7890A Series GC system. Non-polar column: BPX5 from SGE, 5% phenyl 95% dimethylpolysiloxan 0.2 mm×0.25 μm×12 m. Carrier gas: helium. Injector temperature: 230° C. Split 1:50. Flow: 1.0 ml/min. Transfer line: 250° C. MS-quadrupol: 160° C. MS-source: 230° C. Injection vol. 1 μl. Ionization mode Electron Impact (El) at 70 eV. GC percentage=rpa (relative peak area).

$^1$H- and $^{13}$C-NMR: Bruker-DPX-400 MHz spectrometer; spectra were recorded at 400 MHz ($^1$H) and 100 MHz ($^{13}$C) respectively in CDCl$_3$; δ in ppm rel. to SiMe$_4$; coupling constants J in 30 Hz.

Starting materials are either commercially available or are prepared easily in 1-2 steps by the chemist skilled in the art from commercial compounds as described in the literature.

Abbreviations

DPEphos=oxydi-2,1-phenylene)bis(diphenylphosphine)
DMAP=N,N-Dimethylpyridin-4-amine
Xanthphos=4,5-Bis(diphenylphosphino)-9,9-dimethylxanthene Example 1: 6-E-Farnesene from E-Nerolidol General Conditions of the Pd-Catalyzed Elimination Via In-Situ Acetates Acetic anhydride (2.6 kg, 25.3 mol) is mixed with E-Nerolidol (1.1 kg, 5 mol) under nitrogen and stirring, followed by tributylamine (1.9 kg, 10.1 mol), DMAP (32 g), DPEphos (1.55 g, 2.9 mmol) and Pd(OAc)$_2$ (0.3 g, 1.25 mmol, 0.025 mol %). The mixture is heated to 115° C., stirred at this temperature for 4 h, then cooled to 70° C. Vacuum (2555 mbar) is applied and excess acetic anhydride distilled at 66° C. head temperature giving 1.9 kg of an acetic anhydride/tributylamine mixture (ratio 83:17). The distillation residue is cooled to 15° C. and a mixture of 32% HCl (1.43 kg) and H$_2$O (1 kg) is added at 15-20° C. under stirring. The 2-phase mixture is heated to 40° C. and extracted with tent-butyl methyl ether (2×2 l). The combined organic layers are washed with 2 kg of water, 0.5 kg brine and saturated NaHCO$_3$ (2.5 l). After partial evaporation of tent-butyl methyl ether, toluene (1 l) is added. Evaporation under reduced pressure gives 999 g of crude Farnesene which is wipe-film-distilled at 105° C./0.3 mbar giving 945 g of 6-E-Farnesene (93% yield) as a 1:2 mixture of α- and β-isomers (purity 90%). The analytical data are identical to the ones described for 6-E-Farnesene, e.g. by E. J. Corey et al. *J. Am. Chem. Soc.* 140, 16909-16913 (2018).

Example 2

Under the general conditions of example 1 the influence of the catalyst/ligand loading on yield and purity of the elimination product 6-E-Farnesene was explored. As shown in table 1 lower catalyst/ligand loadings than 0.02 mol % Pd(OAc)$_2$ and 0.05% DPEphos are possible giving similar and only slightly lower yields and purities.

TABLE 1

Influence of catalyst/ligand loadings on yield and purity of 6-E-Farnesene.

| run | scale Nerolidol | Pd(OAc)$_2$/ DPEphos$^a$ | time | Farnesyl acetate$^b$ | Farnesene$^b$ | ratio α/β Farnesene puri- ty$^{b,d}$ | Farnesene yield istd$^c$ |
|---|---|---|---|---|---|---|---|
| 1 | 111 g | 200/500 | 5 h | 2% | 32:66 | 98% | 83% |
| 2 | 25 g | 200/500 | 5 h | 6% | 29:66 | 94% | 85% |
| 3 | 2.5 g | 100/250 | 1 h | 10% | 25:64 | 89% | 80% |
| 4 | 2.5 g | 50/125 | 3 h | 13% | 24:63 | 87% | 79% |

General conditions as in example 1 but lower E-Nerolidol scale. All runs at 115° C. and with 97-100% conversion of Nerolidol, except run 4 (97%). a) mol ppm. b) GC rpa. c) internal standard tridecane added to crude product. d) 6-E-Farnesene α+β.

Example 3

Under the general conditions of example 1 the influence of the bisphosphine ligand on yield and purity of the elimination product 6-E-Farnesene was explored. As shown in tables 2 and 3 other bisphosphine ligands such as dpppe and dppf give similar and only slightly lower yields and purities. Bisphosphine ligands BINAP, dppb and dppe and monodentate ligand triphenylphosphine (TPP) give lower yields and purities.

TABLE 2

Influence of ligand at 0.02 mol % Pd(OAc)$_2$ and 0.05% bisphosphine loading.

| run | ligand$^a$ | time | Allo-farne-sene$^{b,d}$ | Farnesyl acetate$^b$ | ratio α/β - Farnesene$^b$ | Farnesene puri-ty$^{b,e}$ | yield istd$^c$ |
|---|---|---|---|---|---|---|---|
| 1 | DPEphos | 5 h |  | 6% | 29:66 | 94% | 85% |
| 2 | dpppe | 7 h | 2% | 9% | 26:61 | 87% | 80% |
| 3 | dppf | 6 h | 3% | 6% | 30:61 | 91% | 82% |

General conditions as in example 1 but 25 g scale of E-Nerolidol. Quantitative conversions. All runs at 115° C. a) 0.02 mol % Pd(OAc)$_2$ and 0.055 mol % ligand. b) GC rpa. c) internal standard tridecane added to crude product. d) Allofarnesene=3,7,11-trimethyldodeca-2,4,6,10-tetraene. e) 6-E-Farnesene α+β.

TABLE 3

Influence of ligand at 0.5 mol % Pd(OAc)$_2$ and 1.2% ligand loading.

| run | ligand [a] | time | Allo-farne-sene [b,d] | ace-tates [b,e] | ratio α/β Farne-sene [b] | Farne-sene puri-ty [b,h] | yield istd [c] |
|---|---|---|---|---|---|---|---|
| 1 | DPEphos | 1.5 h | 4% | | 26:70 | 96% | 81% |
| 2 | dpppe | 2 h | | | 46:51 | 97% | 76% |
| 3 | dppf | 1 h | 2% | | 38:56 | 94% | 75% |
| 4 | dppb | 2 h | 4% | | 45:51 | 96% | 68% |
| 5 | BINAP | 2.5 h | | | 42:54 | 96% | 74% |
| 6 | dppe | 6 h | 3% | 17% [e] | 29:47 | 76% | 69% |
| 7 | TPP [g] | 3 h | 7% | 12% [f] | 41:41 | 82% | 45% |

General conditions as in example 1 but 2.5 g scale of E-Nerolidol. All runs at 115° C. Quantitative conversions of E-Nerolidol, except in run 3 (97%). a) 0.02 mol % Pd(OAc)$_2$ and 0.055 mol % ligand. b) GC rpa. c) internal standard tridecane added to crude product. d) Allofarnesene=3,7,11-trimethyldodeca-2,4,6,10-tetraene. e) E-Nerolidol acetate. f) Farnesyl acetate. g) 2.5 mol % PPh$_3$ ligand. h) 6-E-Farnesene α+β.

Example 4

Under the general conditions of example 1 the influence of the Palladium catalyst precursor was examined. As shown in table 4 combinations of Pd(0) and Pd(II) precursors with ligand DPEphos catalyzed the elimination of E-Nerolidol to 6-E-Farnesene with similar and with slightly lower yields and purities at lower catalyst loadings (Table 5).

TABLE 4

Influence of the Pd-catalyst precursor at 0.5 mol % Palladium catalyst and 1.25% DPEphos loading.

| run | Pd-precursor [a] | Allofarnesene [d] | ratio α/β-Farnesene [b] | Farnesene purity [b,e] | yield istd [c] |
|---|---|---|---|---|---|
| 1 | Pd(OAc)$_2$ | 4% | 26:70 | 96% | 81% |
| 2 | Pd$_2$(dba)$_3$ | 3% | 33:57 | 90% | 78% |
| 3 | Pd/C | | 43:57 | 99% | 82% |

General conditions as in example 1 but 2.5 g scale of E-Nerolidol. All runs 1.5 h at 115° C. and with quantitative conversion of E-Nerolidol except run 2 (97%). a) 0.5 mol % Pd(OAc)$_2$ and 1.25 mol % DPEphos. b) GC rpa. c) internal standard tridecane added to the crude elimination product. d) Allofarnesene=3,7,11-trimethyldodeca-2,4,6,10-tetraene. e) 6-E-Farnesene α+β.

TABLE 5

Influence of the Pd-catalyst precursor at 0.1 mol % Palladium catalyst and 0.25% DPEphos loading.

| run | Pd precursor [a] | Allo-farnesene [d] | Farnesyl acetate [b] | ratio α/β Farnesene [b] | Farnesene purity [b,e] | yield istd [c] |
|---|---|---|---|---|---|---|
| 1 | Pd(OAc)$_2$ | 4% | | 40:57 | 97% | 81% |
| 2 | Pd/C | | 7% | 27:59 | 86% | 78% |

General conditions as in example 1 but 2.5 g scale of E-Nerolidol. All runs 2 h at 115° C. with 98-100% conversion of Nerolidol. a) 0.1 mol % Pd(OAc)$_2$ or Pd/C and 0.25 mol % DPEphos. b) GC rpa. c) Internal standard tridecane added to the crude elimination product. d) Allofarnesene=3,7,11-trimethyldodeca-2,4,6,10-tetraene. e) 6-E-Farnesene α+β.

Example 5: E-Homomyrcene from Homolinalool

Under the general conditions of example 1 acetic anhydride (44.6 g, 437 mmol) and 4,8-dimethylnona-2,7-dien-4-ol (Homolinalool, 15.1 g, 87 mmol) are mixed under itrogen and stirring, followed by tributylamine (32.4 g, 175 mmol), DMAP (0.53 g, 4.4 mmol), DPEphos (59 mg, 0.11 mmol) and Pd(OAc)$_2$ (9.8 g, 0.045 mmol, 0.05 mol %). After heating to 115° C., stirring at this temperature for 3 h and cooling to r.t. the biphasic reaction mixture is poured upon 2 M HCl and extracted with tent-butyl methyl ether. The combined organic layers are washed with water and conc. NaHCO$_3$ and are dried over MgSO$_4$, filtered and evaporated under reduced pressure. The clear brown residue (16 g) is distilled at 50-100° C./43 mbar giving 12.3 g of a fraction containing 69% E-Homomyrcene and 25% 2-E-Methylocimene (4-EZ ratio 1:1). For analytical data of E-Homomyrcene see for example B.Hauer et al. *Nat. Chem. Biol.* 13, 275-281 (2017). Analytical data of (2E)-4,8-dimethylnona-2,4,7-triene (2-E-Methylocimene):

$^1$H-NMR (400 MHz, CDCl$_3$) of the 2E,4E-isomer: δ (ppm)=6.06 (m,1H), 5.57 (dq, J=15.8, 6.6 Hz, 1H), 5.31 (t, J=7.4 Hz, 1H), 5.11 (m, 1H), 2.79 (t, J=7.2 Hz, 2H), 1.75 (m, 3H), 1.74 (m, 3H), 1.69 (m, 3H), 1.63 (m, 3H). $^1$H-NMR (400 MHz, CDCl$_3$) of the 2E,4Z-isomer: 6.47 (m, 1H), 5.69 (dq, J=15.4, 6.8 Hz, 1H), 5.19 (t, J=7.5 Hz, 1H), 5.11 (m, 1H), 2.83 (t, J=7.1 Hz, 2H), 1.81 (dd, J=6.6, 1.2 Hz, 3H), 1.79 (m, 3H), 1.69 (m, 3H), 1.64 (m, 3H).

$^{13}$C-NMR (100 MHz, CDCl$_3$) of the 2E,4E-isomer: δ (ppm)=136.0 (d), 133.3, 131.7, 128.6 (d), 122.6 (d), 122.0 (d), 27.2 (t), 25.6, 18.1 (q), 17.7, 12.3 (q) ppm. $^{13}$C-NMR (100 MHz, CDCl$_3$) of the 2E,4Z-isomer: δ (ppm)=131.7, 131.6, 128.4 (d), 126.8 (d), 125.2 (d), 122.9 (d), 26.4 (t), 25.6, 20.5 (q), 18.6 (q), 17.7 ppm.

GCMS: Homomyrcene: 69% (rpa), t$_R$: 4.61 min (EI$^+$-MS): m/z=150 [M]$^+$ (3%), 135 [M$^+$-CH$_3$] (5%), 121 (2%), 108 (9%), 107 (100%), 93 (8%), 91 (12%), 79 (27%), 69 (42%), 67 (11%), 53 (11%), 41 (58%), 39 (21%). (2E,4Z)-Methylocimene: 12% (rpa), t$_R$: 5.0 min, (EI$^+$-MS): m/z=150 [M]$^+$ (7%), 135 [M$^+$-CH$_3$] (22%), 121 (11%), 119 (8%), 108 (9%), 107 (100%), 106 (23%), 105 (22%), 94 (12%), 93 (28%), 91 (43%), 79 (28%), 77 (20%), 67 (13%), 55 (12%), 53 (11%), 43 (13%), 41 (34%), 39 (26%). (2E,4E)-Methylocimene: 13% (rpa), t$_R$: 5.2 min, (EI$^+$-MS): m/z=150 [M]$^+$ (12%), 135 [M$^+$-CH$_3$] (30%), 121 (12%), 119 (10%), 108 (9%), 107 (100%), 106 (12%), 105 (25%), 94 (29%), 93 (32%), 91 (48%), 79 (30%), 77 (22%), 67 (14%), 55 (15%), 53 (14%), 43 (14%), 41 (41%), 39 (32%).

IR (film/ATR) of an isolated 2-E-Methylocimene sample with 4EZ 2:1: 3028 (w), 2968 (m), 2914 (m), 2882 (w), 2857 (w), 1445 (m), 1376 (m), 1111 (w), 1100 (w), 960 (s), 859 (w), 831 (w), 780 (w), 755 (w).

Example 6: Ethyl Myrcene from Ethyl Linalool

Under the general conditions of example 1 acetic anhydride (303 g, 3 mol) and Ethyl linalool (100 g, 0.6 mol) are mixed under nitrogen and stirring, followed by triethylamine (120 g, 1.2 mol), DMAP (3.6 g, 30 mmol), DPEphos (160 mg, 0.3 mmol) and Pd(OAc)$_2$ (27 mg, 0.12 mmol, 0.02 mol %). After heating to 115° C., stirring at this temperature for 1.5 h and cooling to r.t. the reaction mixture is poured upon 2 M HCl and extracted with tert-butyl methyl ether.

The combined organic layers are washed with water and sat. NaHCO$_3$, water and brine. After drying over MgSO$_4$, filtration and evaporation under reduced pressure the clear brown residue (88 g) is distilled at 30° C./0.04 mbar giving 60 g (67%) of ethyl myrcene with a purity of 77% (EZ ratio 53:24) plus three 3,7-dimethylnona-1,3,6-triene regioisomers (ethyl ocimene with rpa 12:6:4). Analytical data:

$^1$H-NMR (400 MHz, CDCl$_3$) of the main-isomer: δ (ppm) =6.4 (m, 1 H), 5.25 (m, 1 H), 5.0-5.2(4 H), 2.0(4 H), 2.0(2 H), 2.65 (s, 3 H), 1.0 (t, 3 H).

$^{13}$C{1H}-NMR (100 MHz, CDCl$_3$) of the main isomer: δ (ppm)=146.2 (s), 139.0 (d), 137.3 (s), 122.5 (d), 115.7 (t), 113.0 (t), 32.3 (t), 31.5 (t), 26.4 (t), 16.0 (q), 12.8 (q).

GCMS (Elk-MS): t$_R$: 4.5 min (24%, Z-isomer), 4.6 min (53%, E-isomer): m/z=150 [M]$^+$ (3%), 135 (1%), 121 (6%), 94 (12%), 93 (100%), 92 (11%), 91 (21%), 79 (20%), 67 (12%), 55 (78%), 53 (12%), 41 (42%), 39 (21%).

Example 7: E-3,7-dimethylocta-5,7-dien-1-yl acetate from E-2,6-dimethyloct-2-ene-1,8-diol Under the general conditions of example 1, acetic anhydride (49 g, 0.475 mol) and E-2,6-dimethyloct-2-ene-1,8-diol (16.4 g, 95 mmol) are mixed under nitrogen and stirring, followed by tributylamine (35.8 g, 0.19 mol), DMAP (0.6 g, 4.7 mmol), DPEphos (0.65 g, 1.2 mmol) and Pd(OAc)$_2$ (0.11, 0.48 mmol, 0.1 mol %). After heating to 115° C., stirring at this temperature for 7 h and cooling to r.t. the reaction mixture is poured upon 2 M HC; and extracted with tert-butyl methyl ether. The combined organic layers are washed with 2 M HCl, water, brine and sat. NaHCO$_3$. After drying over MgSO$_4$, filtration and evaporation under reduced pressure the orange residue (21 g) is distilled at 70° C./0.02 mbar giving 14 g (69%) of E-3,7-dimethylocta-5,7-dien-1-yl acetate with a purity of 90%. Analytical data:

$^1$H-NMR (400 MHz, CDCl$_3$): δ (ppm)=6.15 (m, 1 H), 6.6-6.7 (m, 1 H), 4.9 (2 H), 4.1-4.2 (2 H), 2.1 (s, 3 H), 2-2.2 (m, 1 H), 1.8 (s, 3 H), 1.7 (2 H), 1.5 (2 H), 0.95 (d, 3 H).

$^{13}$C{1H}-NMR (100 MHz, CDCl$_3$: δ (ppm)=171.2 (s), 142.0 (s), 134.5 (d), 128.5 (d), 114.5 (t), 62.9 (t), 48.6 (t), 35.0 (t), 30.3 (d), 20.3 (q), 19.4 (q), 18.7 (q).

GCMS (El$^+$-MS): m/z=196 [M]$^+$ (0.2%), 181 (0.2%), 163 (0.2%), 153 (1%), 136 (21%), 121 (92%), 109 (8%), 108 (17%), 107 (23%), 94 (22%), 93 (65%), 81 (27%), 79 (35%), 68 (11%), 67 (13%), 55 (41%), 49 (16%), 43 (100%), 41 (23%).

Example 8: Elimination of a mixture of 3,7-dimethyloct-5-ene-1,7-diol and 3,7-dimethyloct-7-ene-1,6-diol Under the general conditions of example 1, acetic anhydride (59.9 g, 0.58 mol) and an equimolar mixture of 3,7-dimethyloct-5-ene-1,7-diol and 3,7-dimethyloct-7-ene-1,6-diol (20 g, 116 mmol) are mixed under nitrogen and stirring, followed by tributylamine (43.7 g, 0.232 mol), DMAP (0.72 g, 5.81 mmol), DPEphos (0.8 g, 1.45 mmol) and Pd(OAc)$_2$ (0.13 g, 0.58 mmol, 0.5 mol %). After heating to 115° C., stirring at this temperature for 5 h and cooling to r.t. the reaction mixture is poured upon 2 M HCl and extracted with tert-butyl methyl ether. The combined organic layers are washed with 2 M HCl, water, brine and sat. NaHCO$_3$. After drying over MgSO$_4$, filtration and evaporation under reduced pressure the clear brown residue (26.5 g) is distilled at 70° C./0.02 mbar giving 19 g (96%) of E-3,7-dimethylocta-5,7-dien-1-yl acetate with a purity of 95%. The analytical data are identical with the ones obtained for this compound in example 7.

Example 9: Elimination of 2,4,8-trimethylnona-2,7-dien-4-ol

Under the general conditions of example 1, acetic anhydride (67 g, 0.65 mol) and 2,4,8-trimethylnona-2,7-dien-4-ol (23.8 g, 131 mmol) are mixed under nitrogen and stirring, followed by triethylamine (26.4 g, 0.26 mol), DMAP (0.8 g, 6.5 mmol), DPEphos (35 mg, 0.065 mmol) and Pd(OAc)$_2$ (5.9 mg, 0.026 mmol, 0.02 mol %). After heating to 115° C., stirring at this temperature for 3.5 h and cooling to r.t. the reaction mixture is poured upon 2 M HCl and extracted with tent-butyl methyl ether. The combined organic layers are washed with 2 M HCl, water, brine and sat. NaHCO$_3$. After drying over MgSO$_4$, filtration and evaporation under reduced pressure the clear brown residue (21.5 g) is distilled at 70° C./0.02 mbar giving 17.8 g (83%) of a mixture of 2,8-dimethyl-4-methylenenona-2,7-diene (exo-isomer) and E-2,4,8-trimethylnona-1,3,7-triene (endo-isomer) (ratio 44:46 rpa, combined purity 90% according to GCMS).

The analytical data of the exo isomer are identical with the ones described for this compound by C.Mazet et al. ACS Catal. 8, 1392 (2018). Analytical data of the endo-isomer 2,4,8-trimethylnona-1,3,7-triene:

$^{13}$C{1H}-NMR (100 MHz, CDCl$_3$): δ (ppm)=142.3 (s), 134.8 (s), 131.6 (s), (d), 126.8 (d), 124.1 (d), 113.7 (t), 40.9 (t), 26.7 (t), 26.6 (q), 23.8 (q), 17.9 (q), 17.7 (q).

GCMS (El$^+$-MS) t$_R$: 5.16 min (44%, exo-isomer), 5.26 min (46%, endo-isomer). m/z of the exo-isomer=164 [M]$^+$ (2%), 149 (8%), 122 (10%), 121 (100%), 107 (10%), 93 (27%), 91 (9%), 79 (18%), 77 (9%), 69 (48%), 67 (12%), 55 (10%), 53 (14%), 41 (60%), 39 (19%). m/z of the endo-isomer=164 [M]$^+$ (2%), 149 (25%), 136 (9%), 121 (32%), 107 (10%), 96 (11%), 95 (31%), 93 (12%), 91 (8%), 79 (13%), 77 (11%), 69 (100%), 67 (32%), 55 (21%), 53 (18%), 41 (77%), 39 (23%).

Example 10: Elimination of Methylgeraniol

General conditions of the Pd-catalyzed elimination via in-situ carbonates.

Sodium methoxide (4.8 g, 9 mmol) is added to water-free Methylgeraniol (505 g, 3 mol) in water-free dimethyl carbonate (811 g, 9 mol) under stirring and nitrogen in a distillation flask equipped with a Vigreux column and a Liebig condenser. The cloudy solution is heated to 110° C. and a methanol/dimethyl carbonate mixture (454 g) is distilled at 40-75° C. head temperature until a final temperature of 100° C. is reached in the distillation flask and nearly quantitative conversion (98%) of methylgeraniol to its carbonate is detected by GC. The mixture is cooled to 60° C. and DPEphos (280 mg, 0.5 mmol) is added. After 10 min stirring Pd(OAc)$_2$ (34 mg, 0.15 mmol, 50 ppm) is added at 60° C. Under strong stirring the cloudy solution is heated to 110° C. and methanol (177 g) is distilled meanwhile the flask temperature raises to 100° C. PEG 400 (86 g) is added and the distillation continued under reduced pressure (20 mbar) giving 410 g (98%) of a homomyrcene/methylocimene/methylgeraniol mixture (GC ratio 69:20:9) at 67° C./20 mbar. Corrected yield of Homomyrcene based on purity: 78%. For analytical data of Homomyrcene see for example B.Hauer et al. *Nat. Chem. Biol.* 13, 275-281 (2017), for the analytical data of the 4EZ-isomers of 2-E-Methylocimene see example 5.

Example 11: 5-methyl-3-methylenehex-1-ene

Sodium methoxide (0.3 g, 5.6 mmol) is added to water-free 3,5-dimethylhex-2-en-1-ol (24 g, 187 mmol) in water-free dimethyl carbonate (50.7 g, 562 mmol) under stirring and nitrogen in a distillation flask equipped with a Vigreux column and a condenser. The solution is heated to 80° C. and a methanol/dimethyl carbonate mixture (40 ml) is distilled at 35-45° C. head temperature and a 85% conversion of 3,5-dimethylhex-2-en-1-ol to its carbonate is detected by GC. The mixture is cooled to 60° C., and DPEphos (0.53 g, 1 mmol) is added. After 10 min stirring Pd(OAc)$_2$ (0.1 g, 0.44 mmol, 0.23 mol %) is added at 60° C. Under stirring the solution is heated to 80° C. and methanol (7 ml) is distilled at 30-35° C. head temperature followed by 7.2 g (37%) of 5-methyl-3-methylenehex-1-ene (exo/endo 89:11).

$^1$H-NMR (400 MHz, CDCl$_3$): δ (ppm)=6.35 (m, 1 H), 5.2 (d, 1 H), 5.07 (2 H), 4.92 (1 H), 2.1 (d, 2 H), 1.8 (m, 1 H), 0.9 (d, 6 H).

$^{13}$C-NMR (100 MHz, CDCl$_3$): δ (ppm)=145.5 (s), 139.1 (d), 116.7 (t), 113.2 (t), 41.5 (t), 26.8 (d), 22.8 (2 q).

GCMS (EI+-MS): m/z=110 [M]+ (14%), 95 (72%), 81 (30%), 68 (100%), 67 (87%), 55 (14%), 53 (28%), 43 (54%), 41 (52%), 39 (32%), 27 (18%).

IR (film/ATR): 2956 (s), 1752 (m), 1594 (w), 1465 (m), 1384 (w), 1267 (s), 991 (m), 894 (s).

Example 12: Elimination of 6,10-dimethylundeca-1,5,9-trien-4-ol

Sodium methoxide (26 mg, 0.46 mmol) is added to water-free 6,10-dimethylundeca-1,5,9-trien-4-ol (30 g, 154 mmol) in water-free dimethyl carbonate (40 ml, 0.5 mol) under stirring and nitrogen in a distillation flask equipped with a condenser. The solution is heated to 97° C. (internal temperature) and a methanol/dimethyl carbonate mixture (22 g) is distilled at 82° C. head temperature. After 3 h another portion of NaOMe is added (26 mg, 0.46 mmol), after 20 h another portion (26 mg, 0.46 mmol), followed by the additon of another portion of dimethyl carbonate (20 ml, 230 mmol) and NaOMe (26 mg, 0.46 mmol). After distillation of more methanol/dimethyl carbonate (7.8 g) at 81° C. head temperature a 98% conversion of 6,10-dimethylundeca-1,5,9-trien-4-ol to its carbonate is detected by GC. DPEphos (0.145 g, 262 mmol) is added and, after 10 min stirring Pd(OAc)$_2$ (20 mg, 0.08 mmol, 0.05 mol %). At 110° C. (102° C. internal temperature) methanol (16.8 g) is distilled at 73° C. head temperature. After 1 h tent-butyl methyl ether and water are added at room temperature, and after phase separation the water phase is extracted with tent-butyl methyl ether. The organic layers are combined, dried over MgSO$_4$, filtered and evaporated giving 27.3 g of crude product (67%, GC rpa) which is purified chromatographically through 100 g SiO$_2$ using tert-butyl methyl ether/heptane 040% as eluent and giving after evaporation 22.7 g of E-10-methyl-6-methyleneundeca-1,4,9-triene (exo) as colorless liquid and with a purity of 73% according to GCMS accompagnied by the endo-isomers (4E,6E)-6,10-dimethylundeca-1,4,6,9-tetraene and (4E,6Z)-6,10-dimethylundeca-1,4,6,9-tetraene (both 22%) which were separated by preparative GC. GCMS-data:

GCMS (EI$^+$-MS) of the exo-isomer (t$_R$ 6.1 min, 73%): m/z=161 ([M-15]$^+$, 1%), 133 (71%), 105 (28%), 93 (17%), 91 (55%), 79 (28%), 77 (18%), 69 (72%), 67 (35%), 55 (11%), 53 (19%), 41 (100%), 39 (30%). (4E,6Z)-6,10-dimethylundeca-1,4,6,9-tetraene (t$_R$ 6.4 min, 9%): m/z=176 (M, 1%), 161 ([M-15]$^+$, 2%), 135 (35%), 133 (10%), 120 (13%), 119 (20%), 107 (42%), 105 (53%), 94 (16%), 93 (100%), 92 (27%), 91 (70%), 79 (37%), 77 (33%), 69 (10%), 67 (27%), 65 (13%), 55 (20%), 53 (18%), 43 (38%), 41 (52%), 39 (29%). (4E,6E)-6,10-dimethylundeca-1,4,6,9-tetraene (t$_R$ 6.7 min, 13%): m/z=176 (M, 5%), 136 (10%), 135 (88%), 133 (10%), 120 (10%), 119 (24%), 117 (10%), 107 (52%), 105 (56%), 94 (11%), 93 (100%), 92 (13%), 91 (80%), 79 (47%), 77 (37%), 69 (10%), 67 (21%), 65 (13%), 55 (24%), 53 (20%), 43 (42%), 41 (59%), 39 (32%).

NMR-Data of the Exo-Isomer $^1$H-NMR (400 MHz, CDCl$_3$): δ (ppm)=1.6 (s, 3 H), 1.7 (s, 3 H), 2.1-2.25 (2 CH$_2$, 4 H), 2.85 (CH$_2$, 2 H), 4.9 (d, 1 H), 5.0 (d, 1 H), 5.1-5.2 (3 H), 5.7-5.8 (m, 1 H), 5.8-5.9 (m, 1 H), 6.1 (d, 1 H).

$^{13}$C{1H}-NMR (100 MHz, CDCl$_3$): δ (ppm)=145.9 (s), 136.7 (d), 133.1 (d), 131.7 (s), 127.2 (d), 124.2 (d), 115.3 (t), 113.8 (t), 36.9 (t), 32.3 (t), 26.9 (t), 25.7 (q), 17.7 (q).

NMR-Data of the Endo-Isomers $^1$H-NMR (400 MHz, C$_6$D$_6$) of (4E,6E)-6,10-dimethylundeca-1,4,6,9-tetraene: δ (ppm)=1.55 (s, 3 H), 1.65 (s, 3 H), 1.7 (s, 3 H), 2.75 (dd, 2 H), 2.8 (dd, 2 H), 4.95-5.1 (2 H), 5.2 (m, 1 H), 5.45 (m, 1 H), 5.55 (m, 1 H), 5.85 (m, 1 H), 6.15 (d, 1 H). (4E,6Z)-6,10-dimethylundeca-1,4,6,9-tetraene: δ (ppm)=1.6 (s, 3 H), 1.65 (s, 3 H), 1.8 (s, 3 H), 2.75 (dd, 2 H), 2.9 (dd, 2 H), 4.95-5.05 (2 H), 5.2 (m, 1 H), 5.35 (m, 1 H), 5.65 (m, 1 H), 5.8 (m, 1 H), 6.65 (d, 1 H).

$^{13}$C{1H}-NMR (100 MHz, C$_6$D$_6$) of (4E,6E)-6,10-dimethylundeca-1,4,6,9-tetraene: δ (ppm)=137.2 (d), 136.3 (d), 133.4 (s), 131.5 (s), 129.8 (d), 124.7 (d), 122.9 (d), 115.1 (t), 37.1 (t), 27.4 (t), 26.7 (q), 17.5 (q), 12.4 (q). (4E,6Z)-6,10-dimethylundeca-1,4,6,9-tetraene: δ (ppm)=136.9 (d), 131.7 (s), 131.4 (s), 128.5 (d), 128.2 (d), 128.0 (d), 123.3 (d), 115.3 (t), 37.6 (t), 26.8 (t), 25.7 (q), 20.8 (q), 17.6 (q).

Example 13: Elimination of 6,10-dimethylundeca-5,9-dien-1-yn-4-ol

Sodium methoxide (4.4 mg, 0.08 mmol) is added to water-free 6,10-dimethylundeca-5,9-dien-1-yn-4-ol (5 g, 26 mmol) in water-free dimethyl carbonate (7 g, 78 mmol) under stirring and nitrogen in a distillation flask equipped with a condenser. The solution is heated to 110° C. and a methanol/dimethyl carbonate mixture (4 ml) is distilled at 76° C. head temperature. After stirring for 23 h a 91% conversion of 6,10-dimethylundeca-5,9-dien-1-yn-4-ol to its carbonate is detected by GC and another portion of sodium methoxide (4.4 mg, 0.08 mmol) and dimethyl carbonate (1.1 ml, 13 mmol) is added. After another 3 h and a 96% conversion DPEphos (24 mg, 0.044 mmol) is added. After 10 min stirring Pd(OAc)$_2$ (3 mg, 0.013 mmol, 0.05 mol %) is added at 100° C. After 4 h stirring at this temperature, water (30 ml) and tert-butyl methyl ether (30 ml) are added at room temperature. Phase separation, extraction with another portion tent-butyl methyl ether (30 ml), washing of the combined organic phases with saturated NaHCO$_3$ (30 ml), drying over MgSO$_4$, filtration and evaporation under reduced pressure gives 4.4 g of crude product containing 45% containing of (E)-10-methyl-6-methyleneundeca-4,9-dien-1-yne and two main impurities (2×9%) of the same molecular weigth (M 174). Flash chromatography through SiO$_2$ using a heptane/tert-butyl methyl ether gradient gives (E)-10-methyl-6-methyleneundeca-4,9-dien-1-yne with a purity of 83%.

$^1$H-NMR (400 MHz, CDCl$_3$): δ (ppm)=1.6 (s, 3 H), 1.7 (s, 3 H), 1.9-2.2 (2 CH$_2$, 4 H), 3.05 (1 H), 5.0 (2 H), 5.1-5.2 (1 H), 5.7 (1 H), 6.35 (1 H).

$^{13}$C{1H}-NMR (100 MHz, CDCl$_3$): δ (ppm)=145.3 (s), 133.8 (d), 131.8 (s), 124.1 (d), 122.6 (d), 114.8 (t), 81.4 (s), 70.3 (d), 32.1 (t), 26.7 (t), 25.7 (q), 21.8 (t), 17.7 (q).

GCMS (EI$^+$-MS): m/z=159 [M-15]$^+$ (3%), 135 (11%), 132 (10%), 131(100%), 129 (10%), 116 (15%), 91 (40%), 77 (12%), 69 (61%), 41 (72%), 39 (25%).

Example 14: 1,3,7-Octatriene from E-octa-2,7-dien-1-ol

Sodium methoxide (6.8 mg, 0.12 mmol) is added to water-free E-octa-2,7-dien-1-ol (5 g, 40 mmol) in water-free dimethyl carbonate (10.8 g, 119 mmol) under stirring and nitrogen in a distillation flask equipped with a condenser. The solution is heated to 100° C. and a methanol/dimethyl carbonate mixture (2.5 ml) is distilled at 63° C. head temperature until a 98% conversion of E-octa-2,7-dien-1-ol to its carbonate is detected by GC. The mixture is cooled to 60° C. and DPEphos (10.9 g, 0.02 mmol) is added. After 10 min stirring Pd(OAc)$_2$ (15 mg, 0.07 mmol, 0.2 mol %) is added at 60° C. Under stirring the solution is heated to 110° C. for 1 h. At r.t. tert-butyl methyl ether and water are added, and after phase separation the water phase is extracted with tent-butyl methyl ether. The organic layers are combined, dried over MgSO$_4$, filtered and evaporated at 70° C./45 mbar giving 3.3 g (78%) of crude Octa-1,3,7-triene with 79% purity and an EZ reatio of 1:1. The analytical data are consistent with the ones in the literature, see for example E. J.Smutny *J. Am. Chem. Soc.* 89, 6793 (1967) and references therein.

$^1$H-NMR (400 MHz, CDCl$_3$) of the EZ mixture: δ (ppm)=2.0-2.35 (2×4 H, CH$_2$), 4.9-5.2 (2×4 H, =CH$_2$), 5.45 (m, 1 H), 5.7 (m, 1 H), 5.8 (m, 2 H), 6.05 (m, 2 H), 6.35 (m, 1 H), 6.65.

$^{13}$C-NMR (100 MHz, CDCl$_3$) of the 3Z-isomer: δ (ppm)=138.1 (d), 137.2 (d), 134.4 (d), 131.3 (d), 115.0 (t), 114.9 (t), 33.3 (t), 31.9 (t). $^{13}$C-NMR (100 MHz, CDCl$_3$) of the 3E-isomer: δ (ppm)=138.0 (d), 132.2 (d), 131.8 (d), 129.6 (d), 117.1 (t), 114.8 (t), 33.7 (t), 27.1 (t).

GCMS (EI$^+$-MS): t$_R$: 2.82 min (39%, Z-isomer), 2.85 min (41%, E-isomer): m/z of the Z-isomer=108 [M]$^+$ (12%), 93 (25%), 79 (8%), 77 (5%), 67 (100%), 65 (20%), 54 (9%), 41 (48%), 39 (41%). m/z of the E-isomer=108 [M]$^+$ (12%), 93 (30%), 80 (8%), 79 (19%), 77 (8%), 67 (100%), 65 (22%), 54 (13%), 41 (49%), 39 (38%), 27 (14%).

(Comparative) Example 15: 1,3,7-Octatriene from E-octa-2,7-dien-1-ol

This example is based on Example 5—Table 1 of JP 2006327960 (Kuraray).

Pd(OAc)$_2$ (45 mg, 0.2 mmol, 0.25 mol %) and PPh$_3$ (0.5 g, 2 mmol) are added to E-octa-2,7-dien-1-ol (10 g, 79 mmol) in xylene (10 ml) under nitrogen and stirring. The yellow reaction mixture is heated to 150° C. (internal temperature 130° C. decreases over time to 110° C.). GC-analysis (rpa, corrected by xylene) after 4 h shows E-octa-2,7-dien-1-ol (36%) and 1,3,7-Octatriene (29%) and after 23 h E-octa-2,7-dien-1-ol (8%) and 1,3,7-Octatriene (55%), At r.t. tert-butyl methyl ether (20 ml) and water (20 ml) are added. After phase separation the aqueous phase is extracted with tent-butyl methyl ether (20 ml). The combined organic layers are dried over MgSO$_4$, filtered and evaporated at 45° C./70 mbar. The residue (15.8 g), analyzed by GCMS (rpa, corrected by xylene, 44%), shows Octa-1,3,7-triene (27%, E/Z 1:2) and E-octa-2,7-dien-1-ol (9%) and unidentified byproducts (54%) at higher retention times. These results are in agreement with example 5 and table 1 in JP 2006327960 (Kuraray): Octa-1,3,7-triene (34%) and E-octa-2,7-dien-1-ol (39%). For analytical data see example 14.

(Comparative) Example 16: Farnesene from E-Nerolidol

This example is based on the conditions of example 11 and JP 2006327960 (Kuraray).

Pd(OAc)$_2$ (26 mg, 0.11 mmol, 0.25 mol %) and PPh$_3$ (0.3 g, 1.1 mmol) are added to E-Nerolidol (10 g, 45 mmol) in xylene (10 ml) under nitrogen and stirring. The yellow reaction mixture is heated to 150° C. (internal temperature 130° C. decreases slightly over time). GC-analysis (rpa, corrected by xylene) after 3 h shows a 10% conversion and after 21 h a 55% conversion of E-Nerolidol. At r.t. tert-butyl methyl ether (20 ml) and water (20 ml) are added. After phase separation the aqueous phase is extracted with tent-butyl methyl ether (20 ml). The combined organic layers are dried over MgSO$_4$, filtered and evaporated. The residue (16.5 g), analyzed by GCMS (rpa, corrected by xylene, 42%), shows 6-E-Farnesene (20%, β:αZ:αE=6:3:11), E-Nerolidol (58%), Allofarnesene (19%) and Farnesol (3%). These results show that selectivity and overall efficiency of the method revealed in JP 20066327960 (Kuraray) is much lower than the one described in example 1.

(Comparative) Example 17: Elimination of E-Nerolidol according to Vorholt

This example is based on the elimination conditions described by Vorholt et al. (*Cat. Sci. & Tech.* 6, 1302, 2016).

Pd(acac)$_2$ (6.2 mg, 0.02 mmol, xanthphos (13 mg, 0.022 mmol) and E-Nerolidol (0.45 g, 2 mmol) are dissolved in a stainless stelle autoclave in toluene (2.5 ml). After addition of trifluoroacetic acid (23 mg, 0.2 mmol) the autoclave is pressurized with 40 bar carbon monoxide and the mixture is stirred at 105° C. for 17 h. After cooling to room temperature the autoclave is vented and flushed with argon. GCMS analysis (rpa) shows complete conversion to 6-E-β-Farnesene (24%), 6E-3Z-Farnesene (28%), 6E-3E-Farnesene (43%), three allofarnesene isomers (5%) and Bisabolene (1%). The yield of 6-E-Farnesene was determined to 71% as analyzed with standard dodecane.

These results show that under acidic conditions a lower yield of 6-E-Farnesene is obtained, compared to the one obtained by Pd-catalyzed elimination under basic conditions as described in example 1.

The invention claimed is:

1. A method for the in-situ formation of a conjugated diene of formula (III) from an allyl alcohol of formula (I), the method comprising converting the allyl alcohol of formula (I)

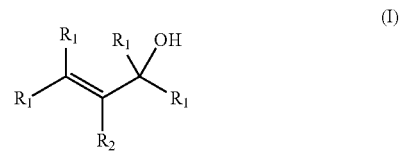

to an allyl carbonate, allyl ester, or allyl formate of formula (II)

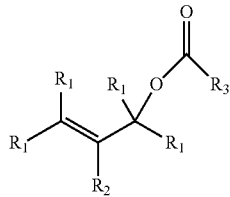
(II)

in the presence of a base followed by converting the allyl carbonate, allyl ester, or allyl formate of formula (II) to the conjugated diene of formula (III)

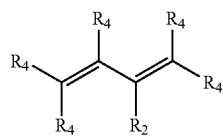
(III)

using a palladium catalyst or palladium catalyst precursor and an organic phosphorous ligand,
wherein
each $R_1$ is independently selected from H, alkyl, substituted alkyl, alkenyl, substituted alkenyl, aromatic hydrocarbon, and substituted aromatic hydrocarbon;
$R_2$ is selected from H, alkyl, substituted alkyl, alkenyl, substituted alkenyl, aromatic hydrocarbon, and substituted aromatic hydrocarbon;
$R_3$ is selected from H, alkyl, substituted alkyl, alkoxy, substituted alkoxy, phenyl, and substituted phenyl;
each $R_4$ is independently selected from H, alkyl, substituted alkyl, alkenyl, substituted alkenyl, aromatic hydrocarbon, and substituted aromatic hydrocarbon; and
wherein at least one $R_1$ bears a proton in a-position of the allylic C3 group which is deprotonated under basic reaction conditions thus forming a diene of formula (III) via 1,2 or 1,4 elimination and the at least one $R_1$ is alkyl, substituted alkyl, alkenyl, substituted alkenyl, aromatic hydrocarbon, or substituted aromatic hydrocarbon.

2. The method of claim 1, wherein each $R_1$ is independently selected from H, alkyl, and alkenyl; $R_2$ is selected from H, alkyl, and alkenyl; $R_3$ is selected from H, alkyl, and alkoxy; and each $R_4$ is independently selected from H, alkyl, and alkenyl.

3. The method of claim 1, wherein the total number of carbon atoms in the compound of formula (I) is from 6 to 40.

4. The method of claim 1, wherein the compound of formula (I) is selected from 2,7-octadiene-1-ol, nerolidol, homolinalool, ethyl linalool, 2,6-dimethyloct-2-ene-1,8-diol, 3,7-dimethyloct-5-ene-1,7-diol, 3,7-dimethyloct-7-ene-1,6-diol, 2,4,8-trimethylnona-2,7-dien-4-ol, methylgeraniol, 3,5-dimethylhex-2-en-1-ol, 6,10-dimethylundeca-1,5,9-trien-4-ol, 6,10-dimethylundeca-5,9-dien-1-yn-4-ol, and 1-(3-hydroxy-3-methylpent-4-en-1-yl)-2,5,5,8a-tetramethyldecahydronaphthalen-2-ol.

5. The method of claim 1, wherein converting the allyl alcohol of formula (I) to the allyl carbonate, allyl ester, or allyl formate of formula (II) in the presence of a base takes place by reacting the allyl alcohol of formula (I) with a compound of formula (IV), a compound of formula (V), or a compound of formula (VI)

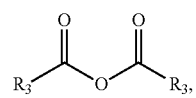
(IV)

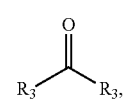
(V)

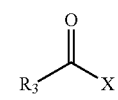
(VI)

wherein X is Cl or Br; and
each $R_3$ is independently selected from H, alkyl, substituted alkyl, alkoxy, substituted alkoxy, phenyl, and substituted phenyl.

6. The method of claim 5, wherein the compound of formula (IV) is acetic anhydride or the compound of formula (V) is dimethyl carbonate.

7. The method of claim 1, wherein the base is selected from triethylamine, tributylamine, dimethylaminopyridine, sodium methoxide, or combinations thereof.

8. The method of claim 1, wherein the palladium catalyst precursor is selected from $Pd(OAc)_2$, Pd $(dba)_2$, $Pd(PPh_3)_4$, or mixtures thereof.

9. The method of claim 1, wherein the organic phosphorous ligand is an organic phosphine ligand.

10. The method of claim 1, wherein the organic phosphorous ligand is selected from (oxydi-2,1-phenylene)bis(diphenylphosphine), 1,5-pentanediylbis [diphenylphosphine], and 1,1'-Bis(diphenylphosphino) ferrocene.

11. The method of claim 1, wherein starting from Formula (I) the yield of the conjugated diene of formula (III) is equal to or greater than about 45%.

12. The method of claim 1, wherein the compound of formula (III) is selected from farnesene, 6-E-farnesene, ethyl myrcene, 5-methyl-3-methylenehex-1-ene, octa-1,3,7-triene, homomyrcene, E-homomyrcene, 2,8-dimethyl-4-methylenenona-2,7-diene, (E)-3,7-dimethylocta-5,7-dien-1-yl acetate, (E)-10-methyl-6-methyleneundeca-1,4,9-triene, and (E)-10-methyl-6-methyleneundeca-4,9-dien-1-yne.

13. The method of claim 1, wherein the total number of carbon atoms in $R_3$ is from 1 to 4.

14. The method of claim 9, wherein the organic phosphorous ligand comprises organic biphosphine ligand.

15. The method of claim 1, wherein the base is selected from amines, alkoxides, alkoxide salts, metal hydrides, and mixtures thereof.

16. The method of claim 8, wherein the palladium catalyst precursor is $Pd(OAc)_2$.

* * * * *